United States Patent [19]
Chance et al.

[11] Patent Number: 5,873,821
[45] Date of Patent: Feb. 23, 1999

[54] LATERALIZATION SPECTROPHOTOMETER

[75] Inventors: Britton Chance, Marathon, Fla.; Claudia S. Robertson, Houston, Tex.

[73] Assignees: Non-Invasive Technology, Inc., Philadelphia, Pa.; Baylor College of Medicine, Houston, Tex.

[21] Appl. No.: 150,084
[22] PCT Filed: May 18, 1992
[86] PCT No.: PCT/US92/04153
  § 371 Date: Nov. 15, 1993
  § 102(e) Date: Nov. 15, 1993
[87] PCT Pub. No.: WO92/20273
  PCT Pub. Date: Nov. 26, 1992
[51] Int. Cl.$^6$ .................................................. A61B 5/00
[52] U.S. Cl. ......................... 600/310; 600/323; 600/331; 600/1
[58] Field of Search ................................ 128/664–5, 633, 128/666; 356/9

[56] References Cited

U.S. PATENT DOCUMENTS

| | | | |
|---|---|---|---|
| 2,790,438 | 4/1957 | Taplin et al. | 128/633 |
| 3,461,856 | 8/1969 | Polyani | 128/633 |
| 4,014,321 | 3/1977 | March | 128/633 |
| 4,029,085 | 6/1977 | DeWitt et al. | 128/633 |
| 4,129,125 | 12/1978 | Lester et al. | |
| 4,167,331 | 9/1979 | Nielsen | 356/39 |
| 4,223,680 | 9/1980 | Jöbsis | 128/633 |
| 4,224,948 | 9/1980 | Cramer et al. | 128/633 |
| 4,266,554 | 5/1981 | Hamaguri | 128/633 |
| 4,281,645 | 8/1981 | Jobis | 128/633 |
| 4,321,930 | 3/1982 | Jobsis et al. | 128/633 |
| 4,380,240 | 4/1983 | Jobsis et al. | 128/633 |
| 4,416,285 | 11/1983 | Shaw et al. | 128/634 |
| 4,452,250 | 6/1984 | Chance | 128/653 |
| 4,469,107 | 9/1984 | Asmar et al. | 128/690 |
| 4,576,173 | 3/1986 | Parker et al. | 128/633 |
| 4,655,225 | 4/1987 | Dahne et al. | 128/633 |
| 4,700,708 | 10/1987 | New, Jr. et al. | 128/633 |
| 4,714,341 | 12/1987 | Hamaguri et al. | 128/633 |
| 4,738,267 | 4/1988 | Lazorthes et al. | 128/748 |

(List continued on next page.)

FOREIGN PATENT DOCUMENTS

| | | |
|---|---|---|
| 0 102 816 | 3/1984 | European Pat. Off. |
| 0 282 234 | 9/1988 | European Pat. Off. |
| 0 488 565 A1 | 6/1992 | European Pat. Off. |
| 2 228 314 | 8/1990 | United Kingdom . |
| WO 90/09003 | 8/1990 | WIPO . |
| WO 92/13598 | 8/1992 | WIPO . |

OTHER PUBLICATIONS

Grinvald et al., "Functional Architecture of Cortex Revealed by Optical Imaging of Intrinsic Signals", Nature vol. 324 pp. 361–364, 1986.

"Watching the Brain at Work", I.E.E.E. Spectrum, vol. 20, No. 3 pp. 52–57, 1983.

Millikan, "Experiments on Muscle Haemoglobin in vivo; the Instantaneous Measurement of Muscle Metabolism", *Proceedings of the Royal Society of London*, vol. 123, 1937, pp. 218–241.

Primary Examiner—Robert L. Nasser
Attorney, Agent, or Firm—Fish & Richardson P.C.

[57] ABSTRACT

The present invention utilizes differential measurement of radiation that migrated into two migration paths between two source-detector pairs placed on the head in a manner that each path is localized in a portion of one hemisphere of the brain. The present invention also provides various embodiments of spectrophotometer systems for in vivo examination of tissue of a human by measuring changes in electromagnetic radiation scattered and absorbed in a migration path in the tissue. Generally, the spectrophotometer systems comprise a light source for introducing the radiation into the tissue, a detector for detecting radiation that has migrated in the tissue, a processor for processing signals of the detected radiation to create processed data, and a system for determining physiological or pathophysiological changes in the tissue of interest. The present invention also provides for determining the metabolic condition of an aerobically stressed portion of tissue such as the muscle tissue of an exercising person.

34 Claims, 21 Drawing Sheets

U.S. PATENT DOCUMENTS

| | | | |
|---|---|---|---|
| 4,773,422 | 9/1988 | Isaacson et al. | 128/633 |
| 4,774,679 | 9/1988 | Carlin | 364/550 |
| 4,800,495 | 1/1989 | Smith | 364/413.03 |
| 4,800,885 | 1/1989 | Johnson | 128/637 |
| 4,805,623 | 2/1989 | Jobsis | 128/633 |
| 4,824,242 | 4/1989 | Frick et al. | 356/41 |
| 4,846,183 | 7/1989 | Martin | 128/633 |
| 4,869,254 | 9/1989 | Stone et al. | 128/633 |
| 4,880,304 | 11/1989 | Jaeb et al. | 356/41 |
| 4,908,762 | 3/1990 | Suzuki et al. | 364/413.09 |
| 4,926,867 | 5/1990 | Kanda et al. | 128/633 |
| 4,972,331 | 11/1990 | Chance | 128/633 |
| 5,032,024 | 7/1991 | Cope | 128/633 |
| 5,062,431 | 11/1991 | Potter . | |
| 5,074,306 | 12/1991 | Green et al. . | |
| 5,088,493 | 2/1992 | Giannini et al. | 128/664 X |
| 5,137,355 | 8/1992 | Barbour et al. . | |
| 5,139,025 | 8/1992 | Lewis et al. | 128/665 |
| 5,213,105 | 5/1993 | Gratton et al. | 128/664 |
| 5,218,962 | 6/1993 | Mannheimer et al. | 128/633 |
| 5,222,495 | 6/1993 | Clarke et al. | 128/664 X |
| 5,253,646 | 10/1993 | Delpy et al. | 128/664 X |
| 5,261,410 | 11/1993 | Alfano et al. . | |
| 5,318,023 | 6/1994 | Vari et al. . | |
| 5,431,170 | 7/1995 | Mathews | 128/633 |

5,873,821

LATERALIZATION SPECTROPHOTOMETER

BACKGROUND OF THE INVENTION

In one aspect, the present invention relates to wearable apparatus for noninvasive determinations of the concentration of oxygen in a specific target region of tissue. More specifically, the present invention discloses a user-wearable system for monitoring the oxygen concentration, or oxygenation trend, in the tissue of a subject undergoing aerobic stress, such as an exercising person.

The increasing popularity of all forms of exercise over the last several decades has also lead to an increased interest in the measurement of individual athletic performance. However, at the present time, athletes are limited to obtaining heartbeat and blood pressure data while they are exercising. Although of some use, these data do not reflect peripheral circulatory capacity or the oxygenation state of specific muscle tissue.

In order to measure oxygen delivery to the capillary bed of the muscles, an athlete must be tethered to electrocardiogram apparatus and have blood samples drawn while running on a treadmill. These are essentially operating room apparatus and procedures, which do not simulate the actual conditions of exercise. The measurement of aerobic efficiency by analyzing the oxygenation state of a particular muscle while exercising is important due to a variety of reasons. For example, as a casual jogger strives to become a marathon runner, the efficiency at which he/she uses oxygen can severely impact performance; data reflecting the utilization of oxygen can provide information which allows an athlete to change pacing strategies or otherwise adjust their activity to produce better results. Other athletes, such as swimmers, cyclists and rowers would also find this information useful for evaluating performance. However, the use of blood oxygenation data is not limited to competitive athletes; even geriatrics who undergo mild aerobic exercise to maintain and improve their health can benefit from data concerning the changes in blood oxygenation brought about by exercise or other activity. Other animals, such as racehorses, can also benefit from this type of performance data. By measuring the oxygen delivery to the muscles, both the quality of training and the natural ability to exercise may be evaluated.

In addition to monitoring and maximizing athletic performance, information pertaining to the delivery of oxygen to the limbs and the brain is important in military and space applications where changes in gravity and other stresses may result in fatigue, and ultimately, blackouts.

Although apparatuses which measure the oxygenation content of blood using data collected from a fingertip or ear lobe are available, these devices do not actually measure the oxygenation state of nearby muscle groups or the brain. To monitor athletic performance, or the condition of exerted muscles, data collection must be performed at the site of interest. For example, runners will wish to be provided with this information during a race, not in a laboratory. Therefore, for an apparatus measuring the metabolic condition of an athlete to be truly useful, a rugged, lightweight, user-wearable system must be provided.

One method by which the oxygen level in a muscle may be measured is tissue spectrometry. For example, red and near-red light, having wavelengths between about 600–800 nanometers (nm), will harmlessly penetrate body tissues. As the light penetrates the tissue, it migrates and is absorbed by deoxygenated hemoglobin in small blood vessels. Normally, tissue receives oxygen from hemoglobin contained in red blood cells, which circulate in the major blood vessels and eventually into the capillary bed, supplying muscle tissue with oxygen. Aerobic activity can cause the level of oxygen use to rise, causing a commensurate rise in the level of deoxyhemoglobin which is compensated for by increased blood flow in trained individuals. Near-red light is absorbed by tissue that is not receiving as much oxygen as the surrounding tissue due to increased levels of deoxyhemoglobin in less trained individuals. Thus, by determining the amount of incident radiation absorbed, the oxygenation state of a specific area of tissue, and the training level of an individual, can be determined.

The present invention also relates to a study of the linkage between cerebral activity and oxygen delivery and oxidative metabolism in the brain tissue. During a brain activity, blood flow can be studied using PET or NMR. Faster electrical and magnetic responses can be measured using EEG and MEG. While these techniques eventually might be able to provide examination and screening for neuronal deterioration and/or deterioration of brain function, they are relatively expensive and not suitable for emergency treatment situations wherein the diagnostic equipment should be taken to a patient. Optical techniques, on the other hand, might provide a suitable, cost effective alternative for examination and screening of a tissue of an organ.

SUMMARY OF THE INVENTION

The present invention provides a novel, wearable system for determining the metabolic condition of an aerobically stressed portion of the muscle tissue of an exercising person. The system comprises a lightweight rugged detector, worn against the skin surface of the subject, adjacent to the muscle being monitored. The system of the present invention thus minimizes any performance impairment. The preferred system further comprises a wearable power pack and a wearable display means for displaying information indicative of the aerobic metabolic condition of the region being monitored. In a preferred embodiment intended for use while running or engaged in similar athletic activities, the display is worn on the wrist and displays information from a leg-mounted detector. In another embodiment, intended to provide information to coaches, a telemetry system is employed to transmit a signal carrying the data from the detector to a remote location, for processing and display.

The detector of the present invention preferably employs a continuous wave spectrophotometer having one or more sources of electromagnetic radiation with wavelengths between about 760 nanometers and about 800 nanometers directed into the tissue of the subject. The detector is efficiently coupled to the body tissue and utilizes the principle of photon migration to detect the portion of the transmitted radiation arriving at an adjacent skin region.

The present invention also discloses methods for displaying the aerobic metabolic condition of a subject. The percentage of deoxyhemoglobin in the blood of the subject is determined, and a signal representative of this percentage is converted into a graphic representation. The display may preferably be a digital display, a bar graph or a series of deoxyhemoglobin levels, placed on a time scale.

OBJECTS AND FEATURES OF THE INVENTION

It is an object of the present invention to provide methods and apparatus which allow a rapid determination of the oxygenation state of tissue, such as muscle tissue, located beneath the surface of the skin of a subject, such as an athlete, without requiring the subject to be tethered or physically connected to laboratory or operating room monitoring equipment.

It is also an object of the present invention to provide apparatus which may be attached to a user which would determine the oxygenation state of a portion of the user's body and provide that information in a readily understandable form.

It is a further object of certain embodiments of the present invention to provide information pertaining to the oxygenation state of tissue directly to a user wearing the apparatus of the present invention.

It is another object of certain embodiments of the present invention to transmit information pertaining to the oxygenation state of tissue to a remote observer.

According to one aspect of the invention, an oximeter is provided for determining the oxygenation state of localized body tissue per se, constructed to be worn over a period of activity by a user and comprising a flexible, body-conformable support member which supports, adjacent the skin of a user, over the localized tissue of interest, at least a pair of spaced apart light sources, and intermediate thereof, at least a pair of wavelength-specific photo detectors, each light source exposed to transmit wavelengths of both of the specific wavelengths toward the localized tissue of interest lying below the skin and below the associated subcutaneous fat layer of the user, and each detector exposed to receive photons of the respective specific wavelength that have originated from each light source, and scattered from the localized tissue and passed back to the detectors through the subcutaneous fat layer and skin of the user, the support member including conformable barrier means disposed between each light source and the detectors, the barrier means being of substance capable of conforming to the contour of the wearer and preventing light energy proceeding laterally in the region of the barrier means from reaching the detectors.

Somewhat more generally, according to another aspect of the invention, an oximeter is provided for determining the oxygenation state of localized body tissue per se, constructed to be worn over a period of activity by a user and comprising a flexible support member which supports, over the localized tissue of interest, at least a pair of spaced apart light sources, and intermediate thereof, at least a pair of wave length-specific light detectors (e.g., photo detectors), each light source exposed to transmit wavelengths of both of the specific wavelengths toward the localized tissue of interest, and each detector exposed to receive photons of the respective specific wavelength that have originated from each light source, and scattered from the localized tissue and passed back to the detectors.

Preferred embodiments of these aspects of the invention have one or more of the following features.

The light sources comprise broad spectrum CW light sources.

The light sources comprise tungsten filament lamps.

The oximeter includes control means for simultaneously flashing the light sources to enable each detector to pick up light energy at its specific wavelength simultaneously from each light source.

Means are provided to flash the light sources at selected intervals unrelated to the interval of heart beats of the user.

According to another aspect of the invention, an oximeter is provided comprising a flexible support member comprised of a molded-elastomeric backing member, the backing member mounting at least one light source means capable of producing one or more (e.g., two) selected wavelengths and oriented to direct the light to tissue of a user and the backing member also mounting detector means capable of separately detecting energy at each of the wavelengths scattered by tissue of the user, integral elastomeric portions of the backing member defining a barrier exposed for conformable contact with an exposed surface of the user, in position to prevent lateral movement of light in subcutaneous layers from the source means to the detector means.

According to another aspect of the invention, an oximeter is provided comprising a flexible support member, the support member mounting at least one light source means capable of producing two selected wavelengths and oriented to direct the light to tissue of a user and the support member mounting detector means capable of separately detecting energy at each of the wavelengths scattered by tissue of the user, the support member supporting a barrier member exposed for conformable contact with an exposed surface of the user in position to prevent lateral movement of light from the source means to the detector means, the barrier comprising a member having an edge sized and positioned to indent skin and the flesh of the user thereby to intercept light migrating laterally in the subcutaneous fat layer and prevent such light from reaching said detector means.

Preferred embodiments of these aspects of the invention have one or more of the following features.

The barrier member is elastomeric, adapted to conform to the contour of the skin of the wearer.

The flexible support member comprises a molded-elastomeric backing member and the barrier member is integral with the backing member.

The member defining the flesh-indenting edge is about 0.5 cm thick in the region that engages the skin.

The barrier member comprises a rib-form member.

There are in series at least one (e.g., two) barrier members, one closely adjacent to the light source means and one closely adjacent to the detector means.

The support member mounts at least one (e.g., two) spaced-apart light sources and at least one (e.g., a pair) of detectors are disposed parallel to each other, disposed laterally relative to the line between the light sources and equal distance from each of the light sources.

The light sources comprise broad spectrum CW light sources.

Electronic control circuitry for the light source and the detector means are provided in which the circuitry is disposed upon a miniature semiconductor chip carried by the support member.

Electronic control circuitry is provided comprised of entirely non-magnetic components enabling use of the device in conjunction with nuclear magnetic resonance imaging.

The oximeter is combined with a real-time readout device constructed to be worn by the user and having a display responsive to the oximeter disposed for viewing by the user.

The oximeter is associated with means securing it to an appendage of the user and the readout device is constructed to be worn by a user.

The oximeter is combined with radio frequency telemetry means for transmitting oximeter data on a real time basis to a station remote from the user or to a receiver in a readout device constructed to be worn by a user.

The oximeter includes electronic control circuitry for the light source and the detector means, the circuitry disposed upon a miniature semiconductor chip carried by the support member in combination with radio frequency telemetry means controlled by the circuitry for transmitting oximeter data on a real time basis to a station remote from the user.

Means are provided for battery-operation of the oximeter and to record oximetry data in internal digital memory for subsequent display or data analysis on a computer.

The oximeter includes electronic control circuitry for the light source and the detector means, the circuitry disposed upon a miniature semiconductor chip carried by the support member, and means for battery-operation of the oximeter and means to record oximetry data in internal digital memory for subsequent display or data analysis on a computer.

According to still another device aspect of the invention, an oximeter is provided comprising a support mounting a light source and detector means at fixed spacing, and electronic control circuitry for the light source and the detector means, the circuitry disposed upon a miniature semiconductor chip carried by the support member, the oximeter encapsulated in biocompatible, water impermeable material, the oximeter constructed and arranged for implantation under the skin of a user for monitoring internal tissue oxygen trends.

The invention also features a number of methods. The method is provided of monitoring the derivative or rate of change of the time based curve representing detected change of tissue oxygen levels and blood volume and employing these rates as a quantitative standard of measurement of tissue oximetry.

The method is provided of assisting an aviator or other person engaged in activity that can subject the person to high G-forces including providing to the person a comfortable oximeter sensor suitable to be worn about the head (e.g., either integrally in a helmet or helmet lining) and capable of responding to tissue oxygen level and blood volume of brain tissue on a real time basis, employing the oximeter sensor to monitor oxygen level of brain tissue of the wearer as the wearer engages in the activity, comparing the monitored value to a standard and generating a signal, such as a warning or control signal, in the event the monitored level(s) violate(s) a pre-established standard.

Preferably, the oximeter is constructed to monitor the trend of oxygen level in the brain, and means are provided to evaluate the rate of change being detected and using the rate of change as the control value and alarm reference.

The method is provided of monitoring a person suspect of sleep apnea or sudden infant death syndrome including providing to the person a comfortable oximeter sensor capable of automatically responding to oxygen level of the person while permitting the person to sleep, automatically monitoring the output of the oximeter by comparing it to a standard and generating a signal, such as a warning or control signal, in the event the monitored level violates a pre-established standard. Preferably the oximeter sensor is taped comfortably to the head for monitoring. Also, preferably the method is used in conjunction with impedance pneumography (breathing rate measurement using chest-wall impedance) and/or EKG to provide an effective in-home apnea monitor to alarm the patient or other individuals in the area so as to wake the patient and prevent hypoxic tissue damage during sleep.

The method is provided of monitoring the cerebral tissue oxygen rate of change as a means of triggering alarm to awaken a subject in danger of infarct due to hypoxia.

The method is provided of monitoring both tissue oxygen level and blood volume in skin flaps such as are produced either by wound or surgery, as the flaps heal, the separation between the source and the detector being established in relation to the thickness of the skin flap to ensure tissue of the flap per se is being monitored.

The method is provided of emergency monitoring of cerebral tissue oxygen level and blood volume in an emergency care situation with the implantable device, in this case, preferably a stand-alone oximeter carried on a backing member with micro-circuitry to monitor the brain or other tissues in peril of damage due to hypoxia.

The method is provided of employing the device of any of the configurations described above wherein the oxygen levels, blood volume and/or rate of charge are measured in cancerous tissue to indicate the activity and viability of the tissue. Also preferably the method includes monitoring of the viability of a tumor following treatment intended to wipe out the cancerous tissue.

Another aspect of the invention is a helmet into which is molded a tissue oximeter in position to engage the head of the wearer when the helmet is put on, the oximeter being of the NIR type, comprising light source means for transmitting near infrared light into the head, detector means held in spaced position relative to the light source means for receiving light scattered by brain tissue and a barrier disposed to engage the head between the light source means and the detector means to prevent light traveling laterally from the light source means from reaching the detector means. Preferably the oximeter has other features described above. In particular, preferably, the oximeter in the helmet includes control circuitry on a miniature chip and preferably means are provided for determining the rate of change of oximetry readings and for comparing the rate of change to a standard and, e.g. producing an appropriate alarm and/or control signal.

Another feature of the invention is a tissue oximeter comprising a support, a detector fixed to the support and a light source mounted in an adjustable manner to the support to enable selection of the spacing between light source and detector for adjusting the mean depth of tissue to which the oximeter responds.

Still another feature of the invention is a tissue oximeter in combination with means connected to receive tissue oxygen readings from the oximeter, and to determine the rate of change of the readings, the rate of change serving as a quantified indication of the state of the charging metabolic process of the tissue.

Another feature of the invention is an oximeter as described, disposed on an endoscope, catheter or guidewire or the like for insertion via a body passage to internal tissue, and including means such as an inflatable balloon to press the oximeter sensor against the localized tissue of interest. Another feature includes providing a water impermeable coating over the device for use in the presence of water.

Somewhat more generally, according to another aspect of the invention, a cognition spectrophotometer system for transcranial examination of brain activity by measuring changes in electromagnetic radiation scattered and absorbed in a migration path in the brain is provided. The cognition system comprises a light source adapted to introduce electromagnetic radiation of a selected wavelength into the brain at an input port placed at a selected location on the exterior of the head; a detector adapted to detect, at a detection port placed at a selected location on the exterior of the head, radiation of the selected wavelength that has migrated in the brain; stimulation means adapted to cause stimulation of a brain activity while introducing the selected wavelength and while detecting radiation at the detection port; processing means adapted to process signals of the detected radiation that has migrated in the brain to create processed data, and evaluation means adapted to determine a characteristic of the brain activity by correlating the processed data with the caused stimulation of the brain activity.

Preferred embodiments of this aspect of the invention have one or more of the following features. Processing means adapted to process detected radiation that has migrated in the brain in the migration path between the input port and the output port being separated by a predetermined distance and being located at different locations on the exterior of the head.

The input port and the output port are located on the frontal bone, parietal bone, temporal bone or occipital bone, wherein the input port and the output port being separated by a predetermined distance in order to localize the migration of the radiation to a selected region of the brain. The predetermined distance can be 4 centimeters.

The system can also have a second light source adapted to introduce electromagnetic radiation of the selected wavelength into the brain at a second input port placed at a second selected location on the exterior of the head; a second detector adapted to detect, at a second detection port placed at a selected location on the exterior of the head, radiation of the selected wavelength that has migrated along the migration path in the brain from the second input port to the second detection port, and processing means adapted to process signals of the detected radiation that has migrated in the brain from the second input port to the second detection port to create second processed data, wherein the evaluation means determine the characteristic of the brain activity by correlating both first mentioned and the second processed data with the caused stimulation of the brain.

This system is adapted to introduce the radiation simultaneously at the two input ports or sequentially at the first input port and detected at the first detection port, and subsequently introduce the radiation at the second input port and detected at the second detection port.

According to another aspect of the invention a cognition spectrophotometer system for transcranial examination of brain activity by measuring changes in electromagnetic radiation scattered and absorbed in a migration path in the brain is provided. The cognition system comprises a first light source and a second light source adapted to introduce electromagnetic radiation of a selected wavelength into the brain simultaneously at a first input port and at a second input port; the first input port and the second input port being placed at a first selected location and a second selected location on the exterior of the head, respectively; a first detector and a second detector adapted to detect simultaneously, at a first detection port placed at a selected location on the exterior of the head, radiation that has migrated in the brain from the first input port to the first detection port and, at a second detection port placed at second selected location on the exterior of the head, radiation that has migrated in the brain from the second input port to the second detection port; stimulation means adapted to cause stimulation of a brain activity while introducing the radiation at the first and second input ports and while detecting radiation at the first and second detection ports; processing means adapted to process signals of the detected radiation that has migrated in the brain to create processed data; and evaluation means adapted to determine a characteristic of the brain activity by correlating the processed data to the caused stimulation of the brain activity.

Preferred embodiments of this aspect of the invention have one or more of the following features. The system has the first input port and the first output port located on one parietal bone (or temporal bone), separated by a predetermined distance, in order to localize migration of the radiation in a selected region of the respective hemisphere of the brain, and the second input port and the second output port located on the other parietal bone (or temporal bone), separated by a predetermined distance, in order to localize migration of the radiation in a selected region of the other hemisphere of the brain.

The system's processing means are further adapted to compare electromagnetic radiation detected at the first and second detection ports to create processed data representing a differential signal.

The processing of the detected radiation can comprise Fourier transformation.

The stimulation means are adapted to cause visual stimulation, acoustic stimulation, or sensorimotor stimulation.

The evaluation means can be adapted to examine pathophysiological properties of the brain tissue or cognitive function of a selected region of the brain based on correlation between the processed data and the caused stimulation of the brain activity.

The system's first and second light sources are tungsten lamps or light emitting diodes. The first or second detectors are silicon diodes or light-to-frequency convertors each with an interference filter adapted to detect the radiation of the selected wavelength.

The processing means comprise differential counter adapted to register differential signals received from the light-to-frequency convertors, clocking means adapted to route signals of the detected radiation from the light-to-frequency convertors to the differential counter, a frequency-to-voltage converter adapted to convert signals from the differential counter and/or a fast Fourier transformer adapted to process differential signal from the frequency-to-voltage converter.

The evaluation means comprise a storage oscilloscope adapted to analyze the Fourier transformed differential signal of the fast Fourier transformer, and/or computational means adapted to analyze the differential signal.

According to another aspect of the invention a cognition spectrophotometer system for transcranial examination of brain activity by measuring changes in light scattered and absorbed in a migration path in the brain is provided. The system comprises the above-described oximeter, stimulation means adapted to cause stimulation of a brain activity while introducing the light using the light source and while detecting the light that migrated in the localized tissue of interest of the brain, processing means adapted to process signals of the detected light that has migrated in the brain to create processed data, and evaluation means adapted to determine a characteristic of the brain activity by correlating the processed data to the caused stimulation of the brain activity.

According to another aspect, the invented system enables examination of a tissue of an organ by measuring changes in electromagnetic radiation scattered and absorbed in a migration path in the organ. The examination is performed by the steps of (a) introducing electromagnetic radiation of a selected wavelength into the organ simultaneously at a first input port and at a second input port; the first input port being placed at a first selected location, and a second selected location, respectively; (b) detecting simultaneously, at a first detection port placed at a selected location on the exterior of the head, radiation that has migrated in the organ from the first input port to the first detection port and, at a second detection port placed at second selected location on the exterior of the organ, radiation that has migrated in the brain from the second input port to the second detection port; (c) processing signals corresponding to radiation detected at the first and second detection port that have migrated in the brain to create first and second processed data, respectively; and (d) determining a selected property of the organ tissues by correlating the processed first and second data.

The organ can be the brain, breast, limb, etc. If the organ is the brain, then the first input port and the first output port are located on one parietal bone (or temporal bone), separated by a predetermined distance, in order to localize migration of the radiation in a selected region of the respective hemisphere of the brain, and the second input port and second output port are located on the other parietal bone (or temporal bone), separated by a predetermined distance, in order to localize migration of the radiation in a selected region of the other hemisphere of the brain.

BRIEF DESCRIPTION OF THE DRAWINGS

FIG. 6b is a longitudinal sideview of the oximeter sensor of FIG. 6a.

FIG. 6c is a longitudinal cross-sectional view taken on line 6c of FIG. 6a;

FIG. 9b is a longitudinal sideview of the oximeter of FIG. 9a;

FIG. 9c is a cross-sectional view taken on line 9c of FIG. 9a;

FIG. 10b is a section of the schematic representation shown in FIG. 10a;

DETAILED DESCRIPTION

Figure 2:
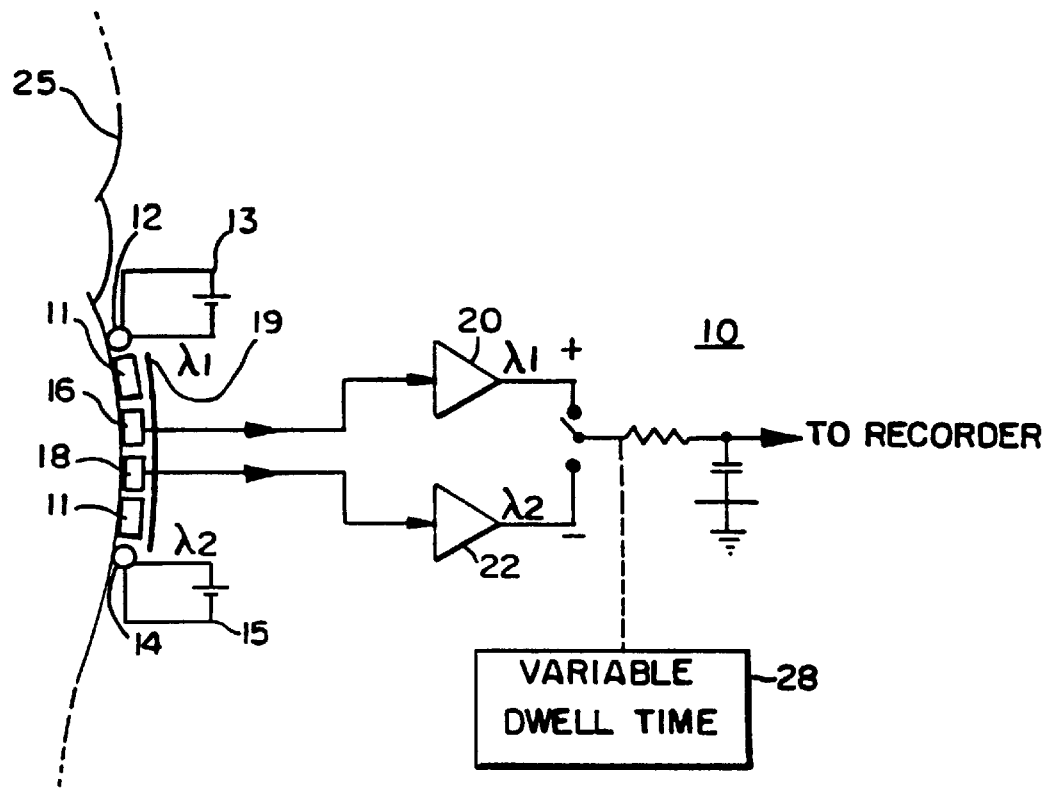
FIG. 2 is a partially diagrammatic, partially schematic representation of a preferred embodiment detector.

A preferred embodiment of the apparatus of the present invention is illustrated in FIG. 2. In this embodiment an electro-optical pickoff detector unit 10 is worn on the leg of the exercising subject 50. It is preferred that the weight of the detector be kept to a minimum so that hindrance to a competing athlete is negligible. In a preferred embodiment, the detector will be housed in a flexible array constructed from a suitable non-irritating, lightweight material.

Power is provided to the detector unit 10 from a replaceable battery pack 30. The replaceable power pack 30 is preferably designed to be of minimal dimensions and weight. Most preferably, the battery pack 30 would be designed to last only for the duration of the activity, e.g., several minutes of sprinting, several hours for a marathon runner, etc. In competitive sports applications, the life of the battery pack is preferably based upon the interval between substitutions or other interruptions between periods of competition.

Figures 1, 1A, 1B:
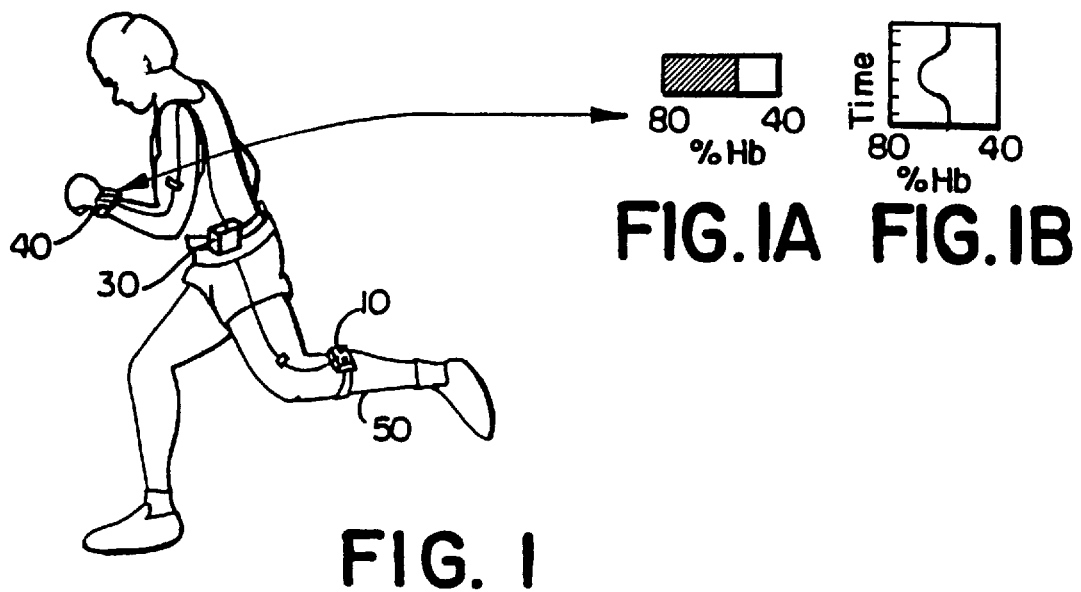
FIGS. 1, 1A and 1B are a depiction of a preferred configuration of an embodiment of the present invention.

The embodiment illustrated in FIG. 1 further comprises an arm indicator 40, which is preferably worn on the arm in the manner of a wristwatch. The arm indicator 40 displays the percentage of deoxyhemoglobin (% Hb) as a measure of the subject's metabolic state. As seen in FIG. 1A, such a display may comprise a simple readout of this information, such as a bar graph. Alternatively, the information displayed may be placed on a time scale, to graphically illustrate the change in % Hb concentration over the course of the activity, as illustrated by FIG. 1B. In a most preferred embodiment, the graphic displays illustrated by FIGS. 1A and 1B are comprised of liquid crystal displays (LCD's), although other electrical or electronic display means may also be used. The amplitude interval of this embodiment is preferably divided into 6–10 levels, each covering a portion of the designated % Hb scale.

It will be appreciated that the range of the % Hb scale may be adjusted depending upon the range expected to occur during the activity. Since the precision of the present invention is limited by that of the indicator, the range which is displayed is an important variable parameter. In the most accurate embodiment of the present invention, with the endpoints of the % Hb scale set at 20% and 40%, the apparatus would have an accuracy of about 6%, which is about the limit of precision which can be obtained from a moving limb. One of ordinary skill will realize that the gain of the apparatus is preset, depending upon the intensity of the activity expected. In a most preferred embodiment, a button placed on the arm indicator 40 allows the gain to be set.

Referring now to FIG. 2, there is illustrated a partially schematic, partially diagrammatic representation of a preferred embodiment of a circuit which comprises the optical pickoff component of a DC tissue spectrophotometer detector 10 contemplated for use in the system of the present invention. The detector 10 is shown for illustrative purposes mounted against a skin surface 25 of a subject. In a typical configuration, the detector is mounted against either large, homogeneous muscles, such as the gastrocnemius or the quadriceps or against the forehead of an adult. Two lamps 12,14 and two detectors 16,18 are contained in a flexible waterproof array. Also contained in the array is an opaque specular barrier, which is a concentric ring of material 11 between the lamps 12,14 and the detectors 16,18 which acts as a barrier zone to light of a specified wavelength. Most preferably, the material which comprises the barrier zone will not only be opaque to light within a specified region, but will further act as an absorber as well. The configuration of dual wavelength light sources combined with a barrier zone is disclosed in "Optical Coupling System for Use in Monitoring Oxygenation State Within Living Tissue," Application Ser. No. 266,116; filed Nov. 2, 1988, which is incorporated herein by reference, as noted above.

Thus, superficial light rays from the skin are, in effect, blocked by the opaque barrier 11 from entering the detectors 16,18. This blocking action by the barrier 11 of these superficial rays enables the system to determine the oxygenation state of hemoglobin within the muscle rather than at the skin surface. The rays that migrate deep within the tissue are received by the detectors 16,18. The light rays that migrate superficially "escape" through the skin surface and will be absorbed by the opaque barrier 11. When, for example, a 760 nm impulse is applied, the deoxygenated hemoglobin (Hb) within the muscle is detected and when an 800 nm signal is applied, the oxygenated and deoxygenated hemoglobin ($HbO_2$ and Hb) within the tissue region are detected. The system is able to ignore the oxygenation state at the skin surface and determine that within the tissue.

The lamps 12,14 may be, for example, ½ W flashlight bulbs that are periodically illuminated in the NR region. The lamps are provided with cutoff filters 13,15 so that only energy of a specified wavelength illuminates the tissue. The silicon diode detectors 16,18 are sensitive to 760±20 nm and 800±20 nm (or 850±20 nm) wavelengths, respectively.

In a preferred embodiment, the lamps 12,14 are light emitting diode (LED) sources, which emit light having a wavelength of about 760±150 anometers and about 800±150 nanometers (or 850±150 nanometers), respectively. In either embodiment, the lamps are flashed or pulsed at a predetermined repetition rate.

The repetition rate of sampling, i.e., the rate at which the lamps are flashed determines the rate at which data may be collected. Thus, for a long distance runner, the lamps are flashed slowly; the output is commensurately changed for a sprinter, the lamps flashed rapidly to produce sufficient data to evaluate an exercise having a duration on the order of seconds. The selection of LEDs as sources of electromagnetic radiation provides a further advantage, since these sources produce a signal-to-noise ratio (S/N) approximately one order of magnitude greater than previously disclosed optical coupling systems using optical light fiber sources.

Figure 4:
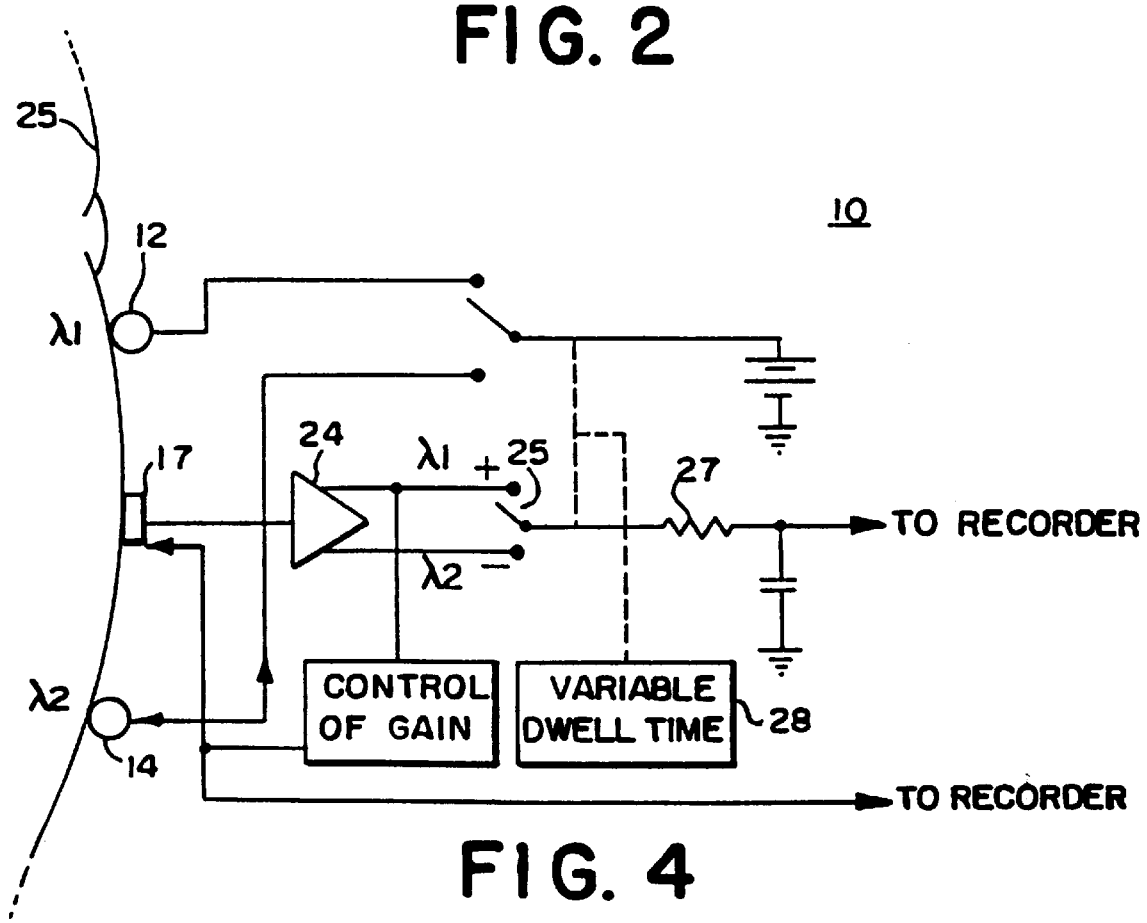
FIG. 4 is a partially diagrammatic, partially schematic representation of an alternate preferred embodiment detector.
Figure 5:
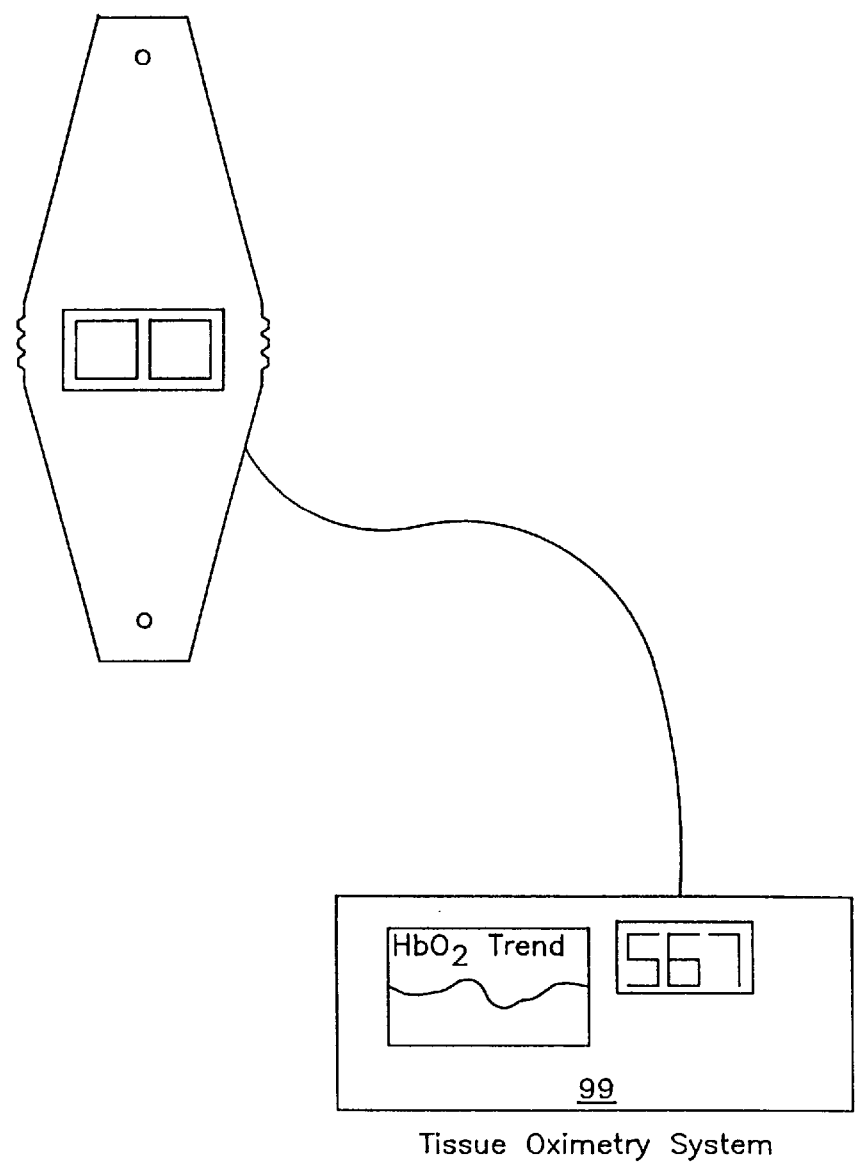
FIG. 5 is a plan view of another preferred embodiment.

Referring now to FIG. 4, an alternate embodiment of a circuit for use with the present invention is illustrated. In this case a single detector 17 responding to separate light flashes collects and transmits signals to an amplifier 24, which has bipolar outputs that are connected intermittently to an integrator 27 by a switch 25. Another switch 26 adjusts the relative duration of the two light pulses to equalize the two signals. One of ordinary skill will understand that those portions of FIG. 2 and FIG. 4 having the same reference numerals perform substantially similar functions. Many details of the particular circuits comprising the present invention need not be set forth with particularity as they are well known or will be obvious to those of ordinary skill.

Referring to FIG. 2, it can be seen that the detectors 16,18 are also protected by a transmitting filter 19 pressed against the skin to minimize the effect of background light. The filter 19 may be comprised of a separate member, a coating or integrated into the housing of the circuit. The DC output of each of the detectors 16,18 is timeshared into its respective differential amplifier 20,22. The amplifiers are connected in opposite polarity, one non-inverting, the other inverting. The dwell time of the switch 23 connecting the amplifiers 20,22 is adjusted to equalize the response of the two signals by appropriate circuitry 28. The signal from the integrator is coupled to a recorder (not illustrated). As shown in FIG. 4, the signal from the 800 nm lamp 12 may be simultaneously employed to vary the gain of the amplifier 24 so as to correct the signals for changes of blood volume and to produce the ratio of the two signals, and thus maintaining constant sensitivity for difference detection. One of ordinary skill will appreciate that a similar gain compensation circuit can be incorporated into the circuitry of the 800 nm detector amplifier 22, shown in FIG. 2. Whether incorporated into the circuits of FIG. 2 or FIG. 4, the 800 nm signal is also coupled to a second recorder channel to collect data reflecting total absorption or blood volume.

Figure 3:
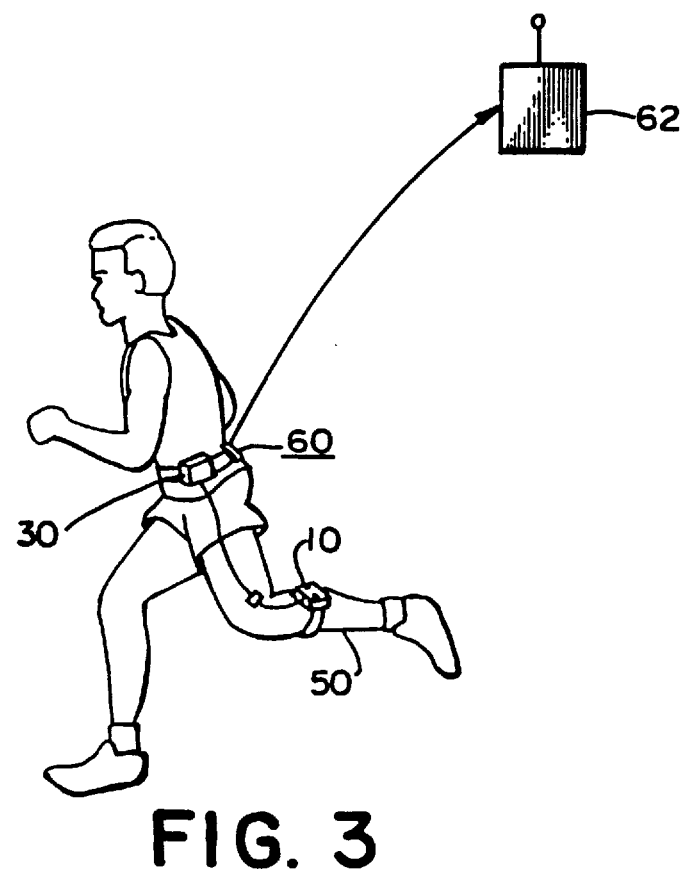
FIG. 3 illustrates another preferred configuration of an embodiment of the present invention.

Another configuration of the present invention is illustrated in FIG. 3. In this embodiment, a radio-linked telemetry system comprised of a transmitter 60 attached to the subject and a receiver 62, allows the remote monitoring of the subject. A supervisor, coach, or clinician is thereby enabled to monitor the performance of the subject. The data display is remote, one of ordinary skill will appreciate that the displays utilized may be similar to those illustrated in FIGS. 1A and 1B, or may be more complex, displaying data using various scales, time overlays, colors, etc. In a most preferred embodiment the telemetry signal would be carried on the 220–400 MHz band, using a transmitter in the 100 MW range.

The configuration illustrated by FIG. 3 allows the present invention to monitor athletes in competition or workers and military/space personnel located in remote locations. For example, the apparatus of the present invention may be used in training to determine the duration of peak performance and the appropriate times for the substitution of fresh players or other adjustments. This configuration would also be preferred for monitoring the metabolic condition of an animal such as a racehorse, racing dog, or any animal whose metabolic condition is being studied for clinical or other purposes. A "postage stamp" oximeter may be provided for, e.g., emergency use, where the oximeter is held to the subject by an adhesive pad positioned peripherally around the device.

In any of the embodiments of the present invention, it is preferred that the data be integrated over at least about ten seconds to smooth out irregularities which normally occur in the concentration of deoxyhemoglobin during exercise. However, it will be understood that the period integration can be varied, depending upon the duration of the activity being monitored.

Although manual balancing of the apparatus of the present invention is required, in a preferred embodiment, the balancing is accomplished by depressing a button, which will normalize the output of the two wavelengths. Automatic balancing performed by an intelligent gain control CPU is also envisioned.

Figure 6A:
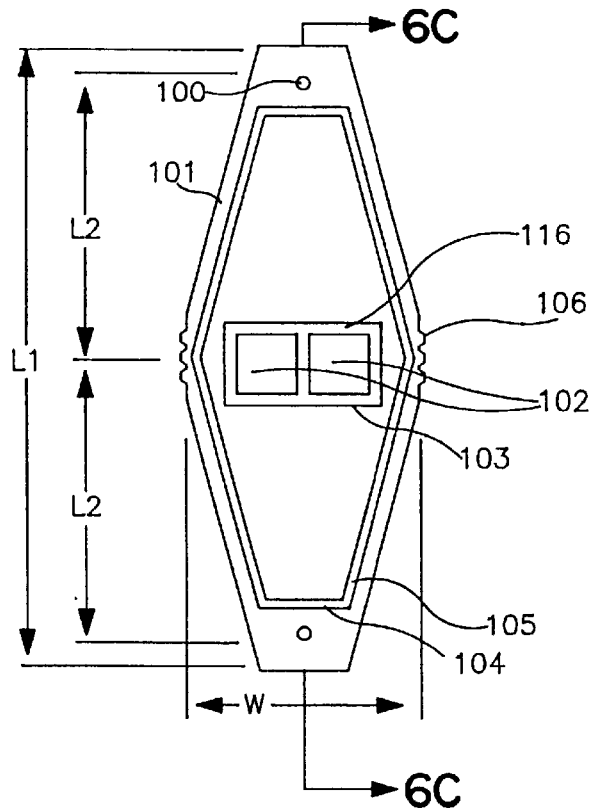
FIG. 6a is a plan view of the oximeter sensor of FIG. 5.
Figure 6B:
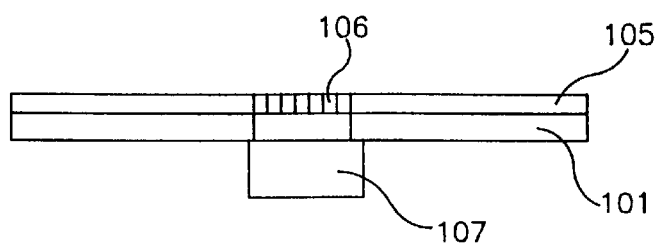
Figure 6C:
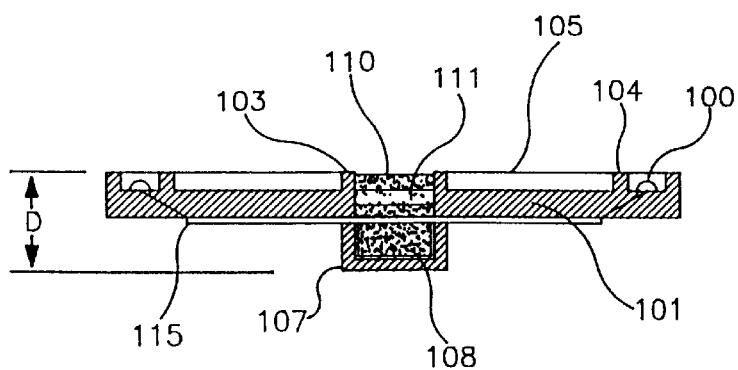

Another preferred embodiment of the oximeter is shown in FIGS. 5 and 6a–6c. A rubber-backing member 101, provides support for two lamps 100 spaced equidistant from two detectors 102 also mounted on backing member 106. The backing member is formed of an opaque, e.g., black, silicone rubber of suitable durometer to enable it to conform to the curvature of the subject part of the human body to which it is applied. For this embodiment, which may be as long ($L_1$) as e.g., 12, especially 8 centimeters, flexure configurations 106 are provided. Light barrier members 103, 104 serve to depress the subcutaneous fat layer and thereby reduce light interference directly between the light sources 100, located at input ports, and the detectors 102, located at detection ports, see description below regarding FIG. 7. Behind the detectors 102 of FIG. 6a, as shown in FIG. 6c, housing 107, defined by the rubber wall, contains the supporting circuitry for these lamps and detectors. As shown in FIG. 6c, narrow band optical filter 110, located at the detection port, lies over photodetector 111, which lies over circuitry 108. Depth D is typically 2 cm. Wiring harness 115 carries power to the lamp.

On the rubber supporting member 101 there are a number of integral raised members 103, 104, 105 and 106. Raised rib 105, which extends about the perimeter, both prevents external light from interfering with the reading and serves to support comfortably the backing member 101 on the subject. Rib 104 extending laterally, adjacent the lamp, and disposed across the line projected between the lamp 100 and the detectors 102, serves as a second light barrier to prevent interfering light transmission between light source 101 and detectors 102. Rib 103 closely surrounds the detectors, and serves as a primary eliminator of environmental light interference, and also serves to absorb light migrating along subcutaneous fat and other subsurface interposed layers, etc. All of these ribs are on the order of ½ centimeter high and ½ centimeter thick. Their outside flesh-engaging edges are rounded for comfort to the wearer. The supporting member 101 and its associated ribs are manufactured in one piece of molded rubber. A suitable mold is provided and black silicone rubber is poured into the mold, cured and dried, leaving the subsequent rubber backing 101 with integral ribs and structures. Suitable mounting sites are provided in the backing into which the detectors 102 and the lamp 100 are mounted during final manufacturing.

The backing member for the oximeter sensor of FIGS. 6a–6c has width, W, length, L1, and depth, D, which may be varied depending upon the application. L2 represents the spacing between light source 100 and the center of detectors 102. Sensors with dimension ($L_2$) from one centimeter to four or five centimeters with corresponding changes in L1 and W are appropriate. One centimeter separation L2 is useful for muscles of very shallow depth while L2 of four or five centimeters is useful for deeper tissue penetration, for example for the brain or other organs.

Small L2 spacings of as low as one centimeter are also appropriate for monitoring tissue flaps, though the best configuration of the sensor for flaps is that shown in FIG. 8c, described below, because flaps are of varying thickness and the adjustability of the device of FIG. 8c enables $L_2$ adjustment proportional to the thickness of the flap. It will also be realized that monitoring may be achieved through wound dressings, bandages, etc.

In the currently preferred embodiment, the light sources 100 are lamps having tungsten filaments, are broad band light sources which eliminating the problem of matching the light sources to the detector filters.

Each detector is comprised of interference filter 110 which blocks out all light except for that which is desired, each of two detectors having a separate wavelength of interest. At this time 760 nm and 850 nm are preferred, although one can envision that changing, depending upon the application. Beneath the filter is a photosensitive detector which picks up the light and transduces it to an electrical signal which is amplified in the circuit 108 and later transmitted to the control circuitry represented in either FIG. 10 or 11.

In the presently preferred embodiment, the interference filter is manufactured by Omega, Inc., and the photodiode beneath it is Part No. F1227-66BR, available from Hamamatsu, having a large sensitive area for favorable signal to noise ratio and an NIR wavelength sensitivity. The sensitive area is approximately 6 millimeters squared.

In the present embodiment the filter and detector are epoxied together around and an electronic shield 115 surrounds the diode/filter pair 110 and 111. This surrounding electronic shield eliminates or reduces extraneous electronic interference. It is presently preferred to form this shield of copper in the form of a windowed box which surrounds the detector filter pair.

Once the two separate filter diode pairs are constructed, they are soldered together and then mounted directly to the circuit board 108. Connected also to circuit board 108 is an ultra low noise operational amplifier with high gain, which converts the current signal from the diodes to a voltage applicable to the control circuitry of FIGS. 10 or 11. The circuit board 108 can be connected via either telemetry or cabling to the oximetry system 99 of FIG. 5, which contains the circuitry shown in FIGS. 10 or 11. Power supply for the amplifier of 108 is supplied by the oximetry system 99 where a cable connection is employed. In other embodiments, a battery is provided for operating the oximeter sensor along with the telemetry system, to be described below in connection with an implantable embodiment.

Figure 7:
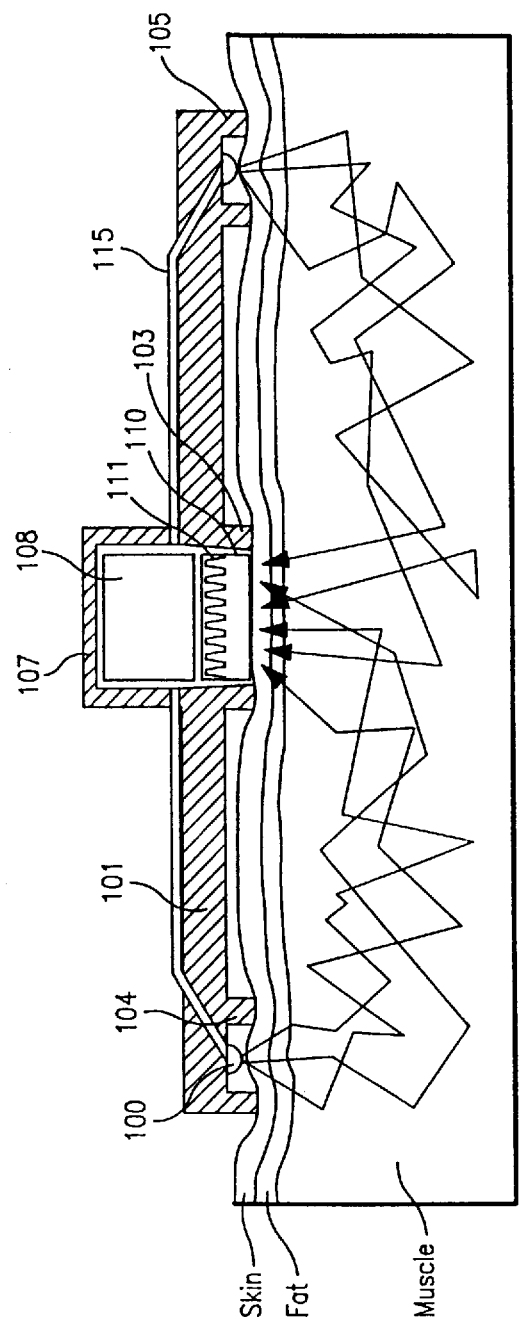
FIG. 7 is a transverse cross-sectional view of a oximeter sensor according to the invention in place upon the flesh of a wearer.

Referring now to FIG. 7, the preferred embodiment of FIGS. 6a–6c is shown diagrammatically as it is placed upon the skin of a subject. The edges of the upstanding rib-form barrier members serve to concentrate pressure upon the skin, depressing the skin layer and the underlying fat layer. The barriers 103 and 104 serve to prevent light from migrating directly between the source 100 and the detectors 102 and because the barriers are placed with pressure upon the surface of the skin, they serve to reduce the area of the fat through which light can pass directly. If one were to imagine the situation without a barrier, one would see light passing almost directly between the source and the photodiodes, the fat layer serving, effectively as a light guide. The absorbing ribs reduce this noise effect. Light which is emitted by the sources 100 enters the skin directly beneath the source, passes through the fat to the underlying tissue, migrates through the tissue, is absorbed, scattered, and eventually is received by the photodiode. The migration path has been described in prior art as a banana-shaped path which is due to the photon migration between the source and the detector. "Banana-shaped" is a mean representation of the photon path, whereas the actual migration path constitutes many scattering changes of direction of the photons as they course between the light source, located at the input port, and the photodiode, located at the detection port.

Figure 8A:
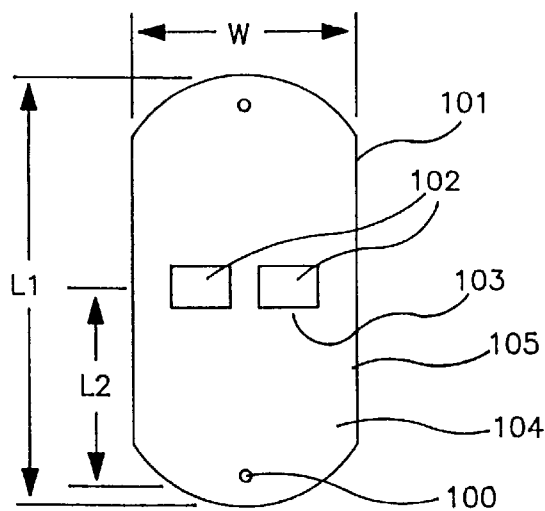
FIGS. 8a, 8b and 8c are plan views of other preferred embodiments of the oximeter sensor.
Figure 8B:
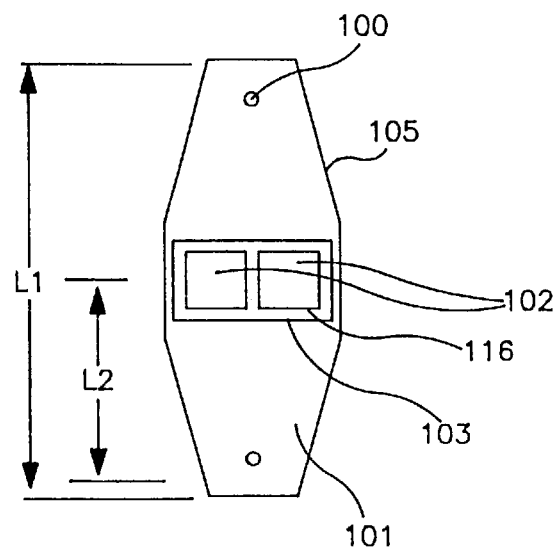
Figure 8C:
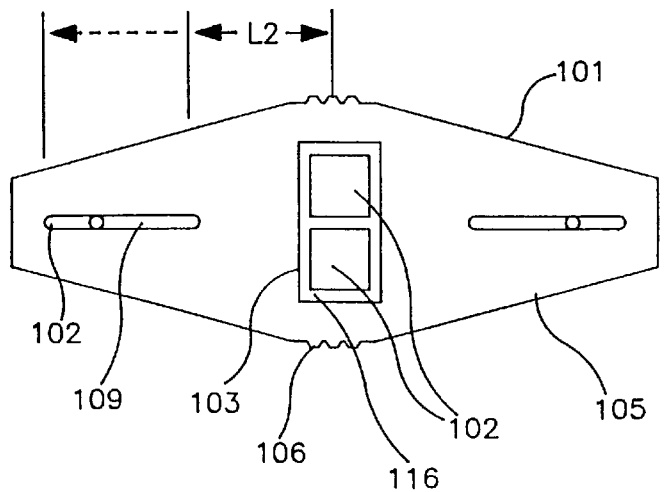

FIG. 8a–8c show alternate preferred embodiments of the oximetry sensor.

The embodiment of FIG. 8a is useful for muscle. It is shown here as a comparison to FIGS. 6a–6c, wherein the overall length L1 and the overall width W depends upon the application and L2 as in FIGS. 6a–6c can vary dependent upon the application from one centimeter or less to five centimeters or more.

The overall length L1 is determined chiefly as a result of the source 100 to detector 102 spacings L2. The spacing determines the depth of penetration of the light which is scattered and migrated through the tissue. The farther the source is from the detector, the deeper the mean penetration. So for shallow penetrations, one would envision a short L2 and thereby L1. The penetration desired depends upon the muscle of interest. For a large muscle, for example, in the thighs or the calf, which tend to be fairly large, one needs a substantial separation to both (a) penetrate the thicker fat layer and (b) to sense deeper into the larger muscle.

For such muscles, a common dimension for L2 would be 3 to 5 centimeters and L1 would thereby be 7 to 11 centimeters.

The width of the sensor is chiefly dependent upon the size of the detectors 102. In the configuration of the presently preferred embodiment wherein each detector has a photo-sensitive area of approximately 6 millimeters squared, the width is dependent almost entirely upon those two dimensions. As the photodetectors reduce in dimension width W decreases.

The larger photodetector units provide better signal to noise ratio and thereby enable more accurate representation of the oxygenation state of the tissue. As improvements in technology occur and better photodetectors and initial amplification circuitry are developed, the detector size will decrease, with consequent decrease in W.

As with FIG. 6a–6c, the supporting member 101 of FIG. 8a carries numerous rib-form barriers. In this case barriers 103, 104 and 105 serve both support and light reduction functions. Perimeter barrier 105 in this case completely surrounds the light source and detector grouping. Between the light source and barrier 103, is barrier 104 on opposite sides of the detectors. Barrier 104, as previously mentioned, serves to reduce light as it travels between source and detector in the subcutaneous layer.

The embodiment of FIG. 8b represents an alternate to that of FIG. 8a wherein the dimensions of FIG. 6a are significantly reduced to achieve a smaller probe. In addition to the backing member 101 being reduced in size, in FIG. 8b, barrier 104 has been eliminated and barrier 103 serves as the primary and only eliminator of both external light and interference between source 100 and detector 102. The typical dimensions for L2 of FIG. 8b would be 3 centimeters or less, L1 being 6 centimeters maximum or less. In comparison, the minimum size for the embodiment of FIGS. 8a and 6a–6c of L2 would be 3 centimeters or greater.

The embodiment pictured in FIG. 8b is suitable to be used for example in neonate applications where the desired tissue volume is extremely small and one needs a small probe. It would also be used for very shallow depth muscle and for example, skin flap measurements where skin flaps are created either by surgery or by wound. The sensor is placed over the skin flap to determine the health of that flap as it heals.

The smaller sensor sizes improve the flexibility of the device to correspond to perhaps smaller target muscles and smaller regions of interest.

Referring to FIG. 8c, a similar embodiment to that of FIG. 6a–6c is shown, but having a light source track 109 to enable variable spacing between the light source 100 and detector. Barrier 103 has been omitted in favor of allowing for user settable variations of L2. L2 may be varied between for example 2 centimeters to say 5 centimeters depending upon the application. This may be used for skin flap work in determining the health of a skin flap as described above, with the distance L2 set in accordance with measurement of the thickness of the skin flap.

For this adjustability, a slide mechanism is employed in manner to keep L2 equal on both sides, in dependent motion such that as the spacing of one varies, the spacing of the other will also change.

The embodiments of FIGS. 5–8 share the desirable features of a parallel pair of detectors 102, side-by-side extending across the line between the light source. By simultaneous flashing of both lamps each detector receives photons at its wavelength from both lamps, simultaneously.

Figure 9A:
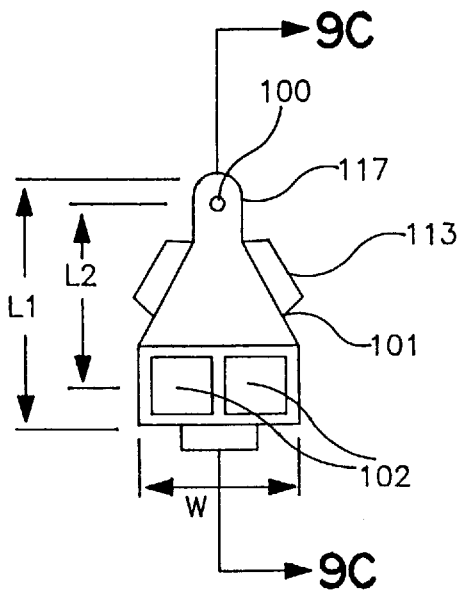
FIG. 9a is a plan view of an implantable oximeter sensor according to the invention.
Figure 9B:
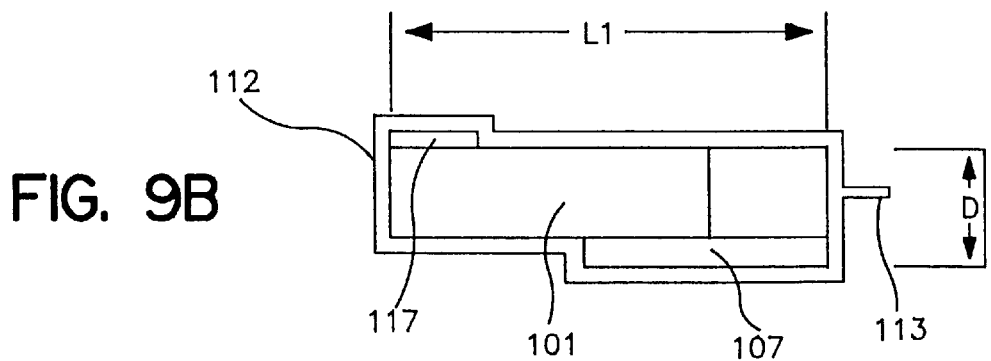

FIG. 9 shows another preferred embodiment of the tissue oximeter sensor, in the form of an implantable probe. To further reduce size, one of the light sources 100 is omitted. As in FIG. 8b, light barrier 104 is omitted. The lone barrier in this case 117 serves to reduce direct light interference.

As previously mentioned, backing member 101 holds in fixed relation the light source 100 and the detectors 102. The length L1 is solely dependent upon a single L2 between the single source and the dual detectors. The spacing depends chiefly upon the muscle location internally of the organ which is being studied. As previously mentioned, from ½ centimeter or 1 centimeter to 5 centimeters may be appropriate, depending upon the application. Applications envisioned are horse muscle studies.

For application, the physician makes an incision in the skin and slips the oximeter sensor underneath the skin and cutaneous fat layer. There are suture points 113, e.g., biocompatible webbing, surrounding the backing member 101. A coating over the entire sensor is comprised of a biocompatible base material 112, which protects the circuitry from the human system, and protects the human from the invasive nature of the circuitry.

Figure 9C:
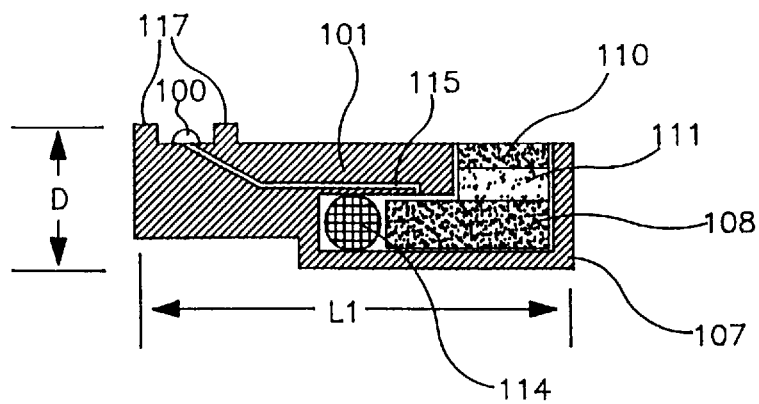

The thickness of the device is of the order of 1 to 2 centimeters maximum. That depth dimension will diminish as technology changes. In FIG. 9c the supporting circuitry is shown. As previously described, the filter/photodiode pair 110, 111 is disposed above the circuit 108. In addition to receiving and amplifying the signal, the circuit shown here is responsible for telemetric communication of the signal to a receiver outside of the body. A battery 114 powers that circuitry.

By employing a radio signal to transmit the information from within the body to a receiver outside the body there is no need for wires and the like puncturing the skin.

Figure 10:
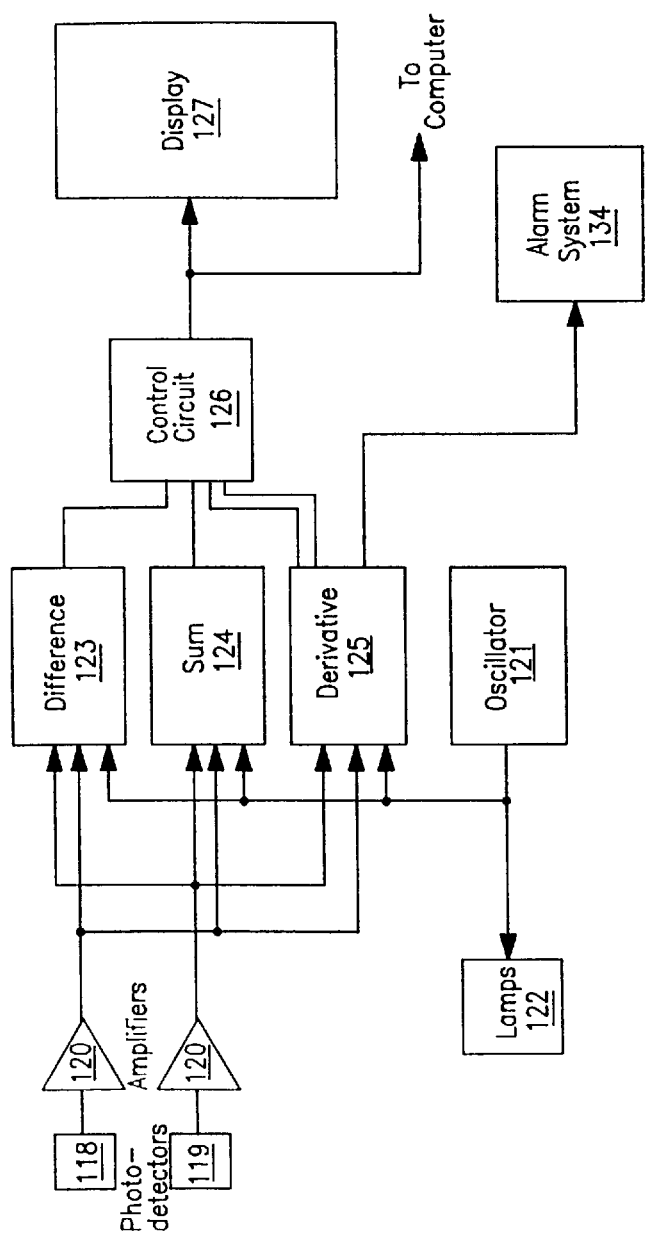
FIG. 10 is a block diagram of an analog version of the control system for the oximeter of the previous figures.
Figure 10A:
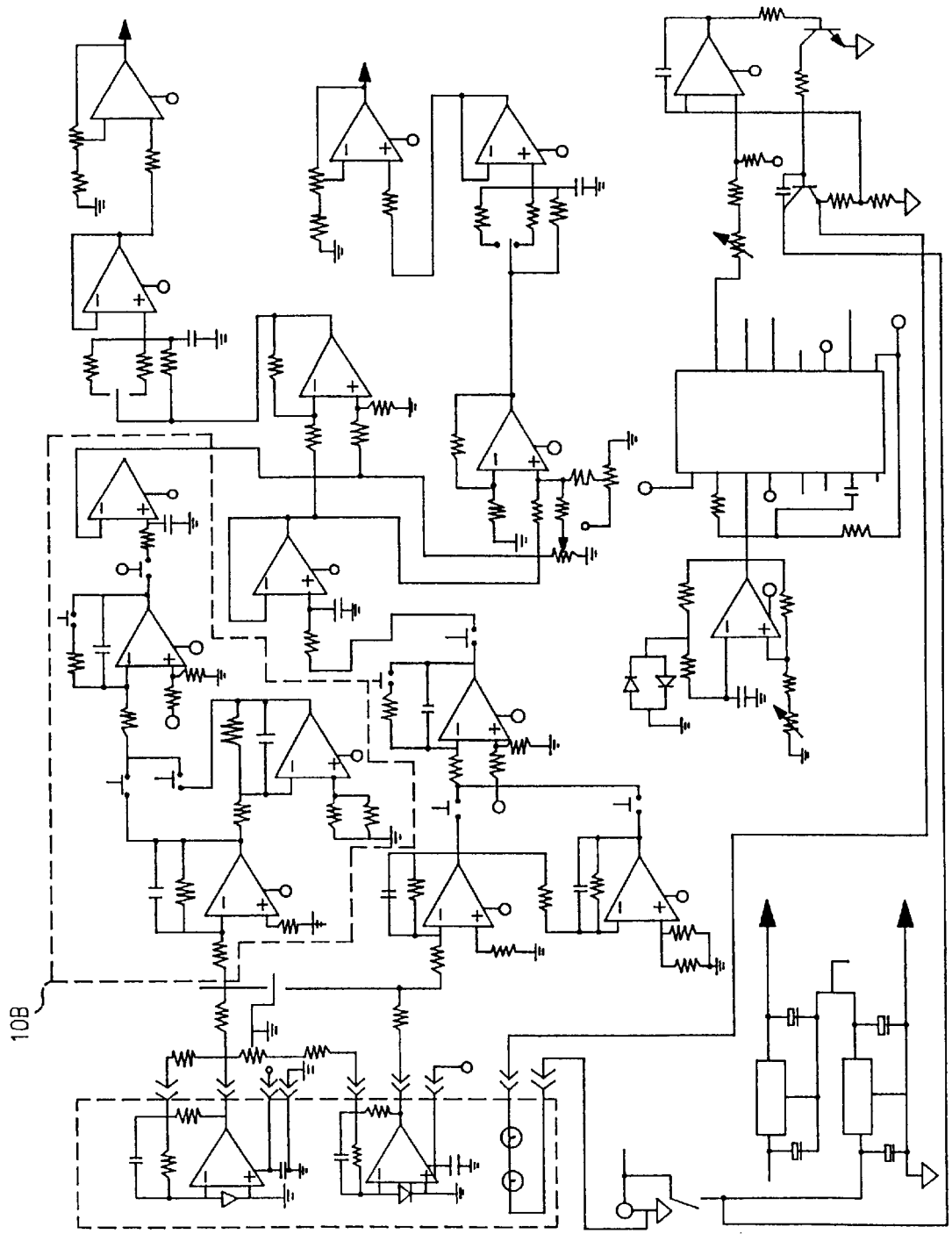
FIG. 10a is a schematic representation of the oximeter control system shown in FIG. 10.

Referring to FIG. 10, one embodiment of the circuitry for driving the device is shown. (Schematic diagram of the embodiment of FIG. 10 is shown in FIG. 10a.) This is an analog circuit wherein the signal from photodetectors 118 and 119 is amplified by amplifiers 120 and sent to three manipulative circuits that take the difference, the sum and the derivative of the signal. The difference 123, as described above, simply subtracts 760 nm minus 850 nm to obtain a signal representing deoxygenation.

The sum circuit 124 takes a weighted sum of the 760 nm and 850 nm signals, weighting being chosen appropriate to the fact that the signal variation due to oxygenation or deoxygenation is greater for 760 nm than it is for 850 nm. Because these contrabestic wavelengths tend to cancel the signal due to the difference in oxygenation, the sum shows independent of the difference and is taken as representative of the blood volume changes in the tissue.

The derivative circuit 125 takes the simple derivative to show the rate of change of both of the signals. This is useful, as described above, to trigger alarm circuitry based upon established standards, wherein the higher the rate of the change, and the more sustained that rate of change, the more potentially dangerous the rate of change. This is useful, as mentioned, for example in monitoring aviators for possible black-out conditions and for apnea.

The outputs of these units 123, 124 and 125 are applied to the control circuit which controls where the signals are directed and how they are displayed and/or sent to a computer. The control circuit may be simply embodied as a switch to switch the output to an LCD display, for example. The analog signal from control circuit can be digitized in the display unit 127 and displayed as a digital number. Additionally it can be digitized and sent to a computer or sent in analog form to a computer for digitization.

The oscillator 121 is an independent source for determining the frequency of lamp flashing. Lamps flash at frequency of ½ Hz or 2 flashes per second or greater. This frequency may be independent of heart rate or any other external factor and is set externally by the user, and may be dependent upon application as mentioned earlier. For example, during exercise, the frequency chosen for the lamp will depend upon the frequency of the exercise, such as the revolutions per minute on a bicycle. If one is expected to encounter a slow change in oxygenation due to the nature of the exercise or the muscle of interest, one can employ a fairly low flashing rate. There is no need for high resolution measure of the rate of change as is required in pulse oximetry.

The lamp rate is tied to the control circuit. The oscillator establishes the timing for the sum and difference circuits because the sum, difference and derivative circuits need to be synchronous. In operation, the lamp flashes, the signal is picked up by the photodetectors and while the lamps are on, the difference, sum and derivative are calculated and are thereby stored in the appropriate memories, and via the control circuit can be directed to the display and to the computer.

The derivative system is the basis of the alarm system. Output from the derivative is compared to a standard within the alarm circuitry, which then determines if there is, for example, a normal rate of change, represented say by a green light, a cautionary rate of change, which may be represented by a yellow light, and a fairly rapid and/or sustained rate of change, which would be for example shown by a red light, an alarm or a buzzer or the like, which would alarm both the wearer or act remotely for example to warn the parents of a neonate in the case of SIDS (Sudden Infant Death Syndrome).

Figure 10B:
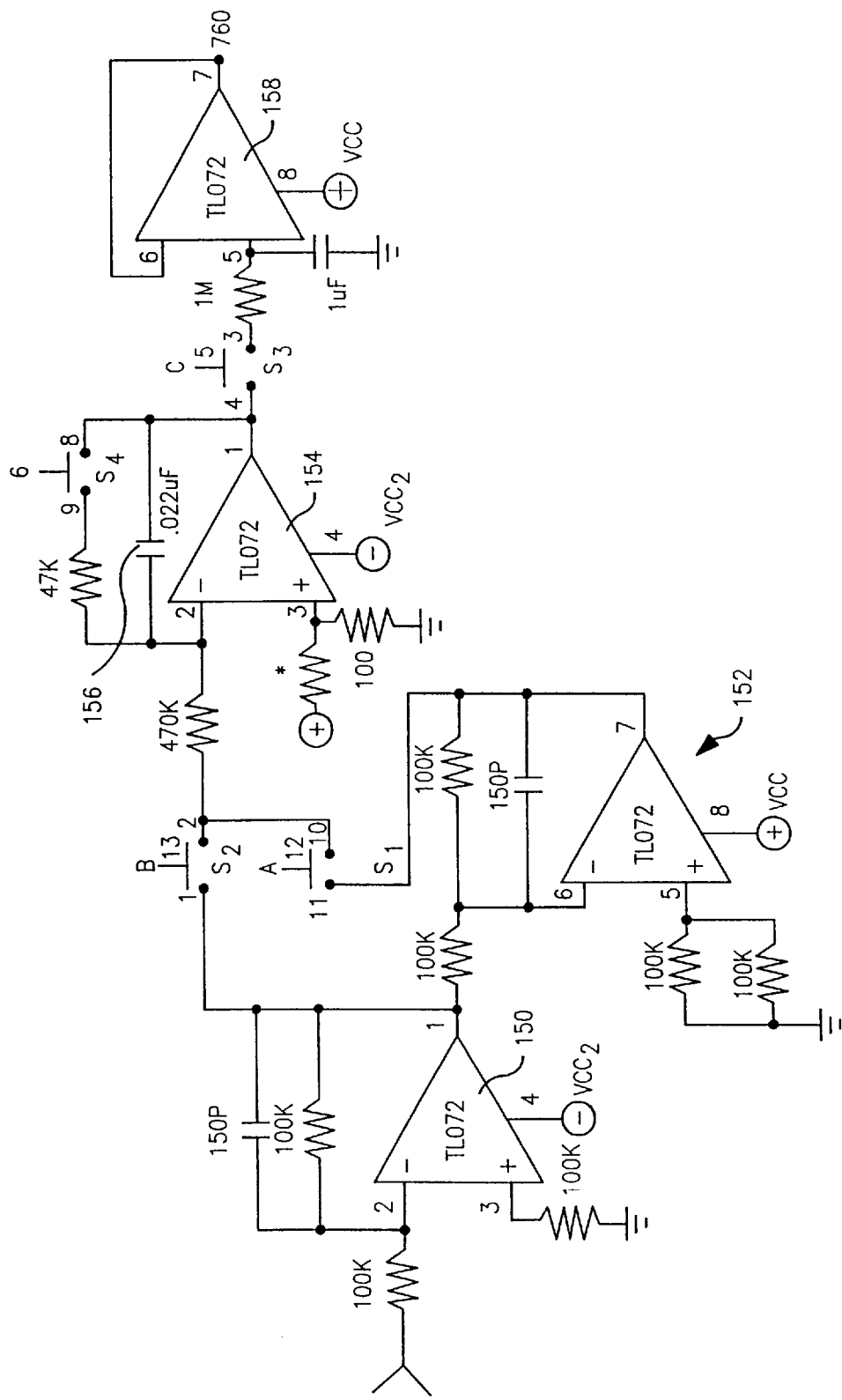

The embodiment shown in FIG. 10a enables correction for the dark current/noise that comprises background light, DC offset of the operational amplifiers, photodiode dark current, temperature effects on the outputs of individual components and variations due to changing environment. The dark current/noise correction is explained on the circuit of FIG. 10b which is a section on the analog circuit, shown in FIG. 10a. The oximeter (FIG. 10) performs data acquisition in four steps which are synchronized by an internal oscillator. In the first step, the lamps are off. The output is directed to an integrator 154 and integration capacitor 156 is charged to the dark level voltage. In the second step, the lamps are turned on. The preamplifier output that corresponds to the intensity of the detected light is directed to integrator 154 in a way to charge capacitor 156 with current of polarity opposite to the polarity of the charging current in the first step. This is achieved using appropriate ON/OFF combination of switches S1 and S2. The voltage of capacitor 156 is charging to a value which, at the end of this step, represents the total signal minus the dark level noise signal. In the third step, both switches S1 and S2 are turned OFF to disconnect both the positive unity gain and the negative unity gain operational amplifiers (150 and 152). Then, the output of integrator A is moved via switch S3 to a hold circuit 158 which also functions as a low pass filter. This output is the detected signal at one wavelength corrected for the background noise. In the fourth step, the switches S1, S2 and S3 are open and switch S4 is closed in order to discharge capacitor 156 through a 47K resistor. At this point, the circuit of integrator 154 is reset to zero and ready for the first step.

Figure 11:
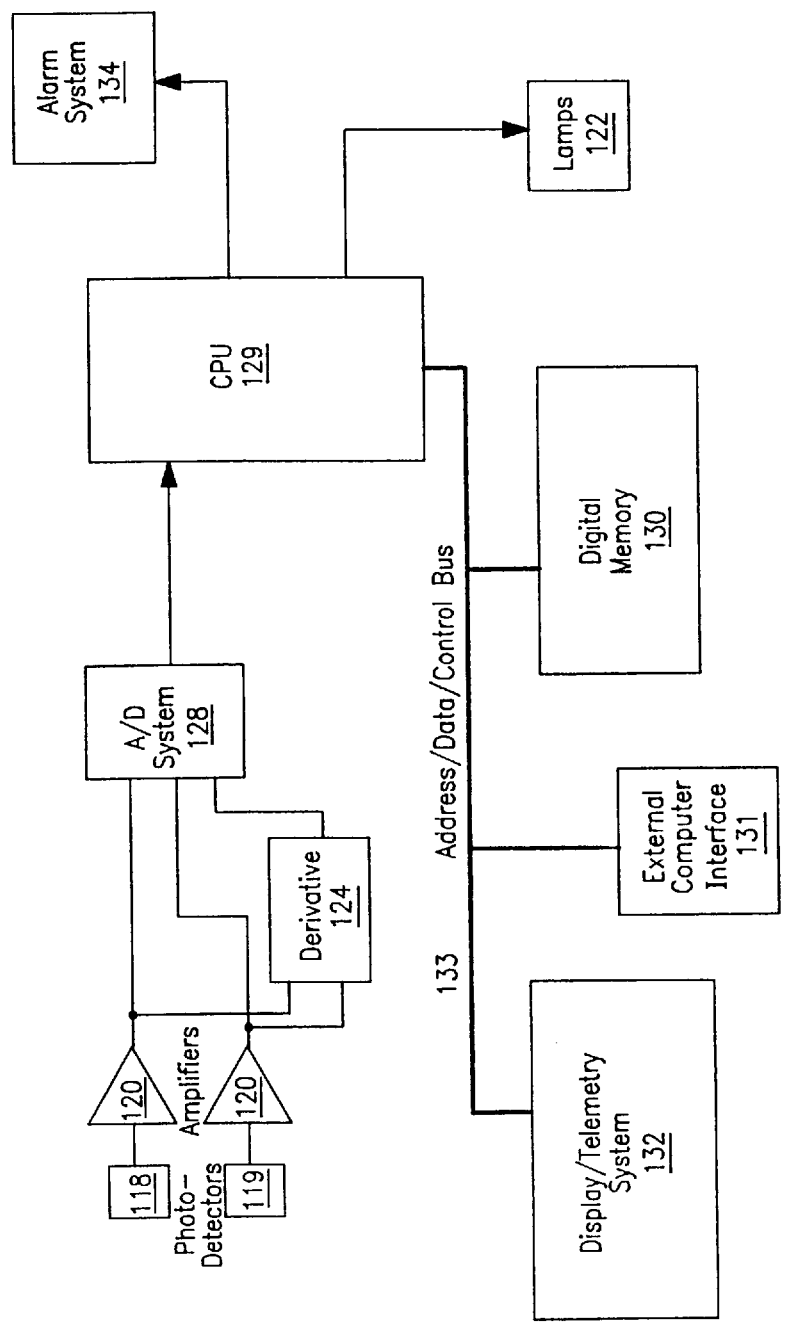
FIG. 11 is a block diagram of a digital version of the control circuit of the oximeter of the previous figures.

In another preferred embodiment, digital version of the circuitry depicted in FIG. 11, the identical photodetectors 118 and 119 and similar amplifiers output signal to an analog to digital conversion system 128 and to a derivative circuit 124. The derivative circuit outputs signal to the analog digital converter, in this case for evaluation by the central processing unit, CPU, or microprocessor 129. Software, shown in FIG. 12, controls the system of data collection and lamp frequency 122 as well as the storing of data, interfacing with external computers and displaying or telemetrically communicating this information. The heart of this circuit is the central processing unit driven by software which collects data, stores it, displays it and sounds alarm if necessary.

Figure 12:
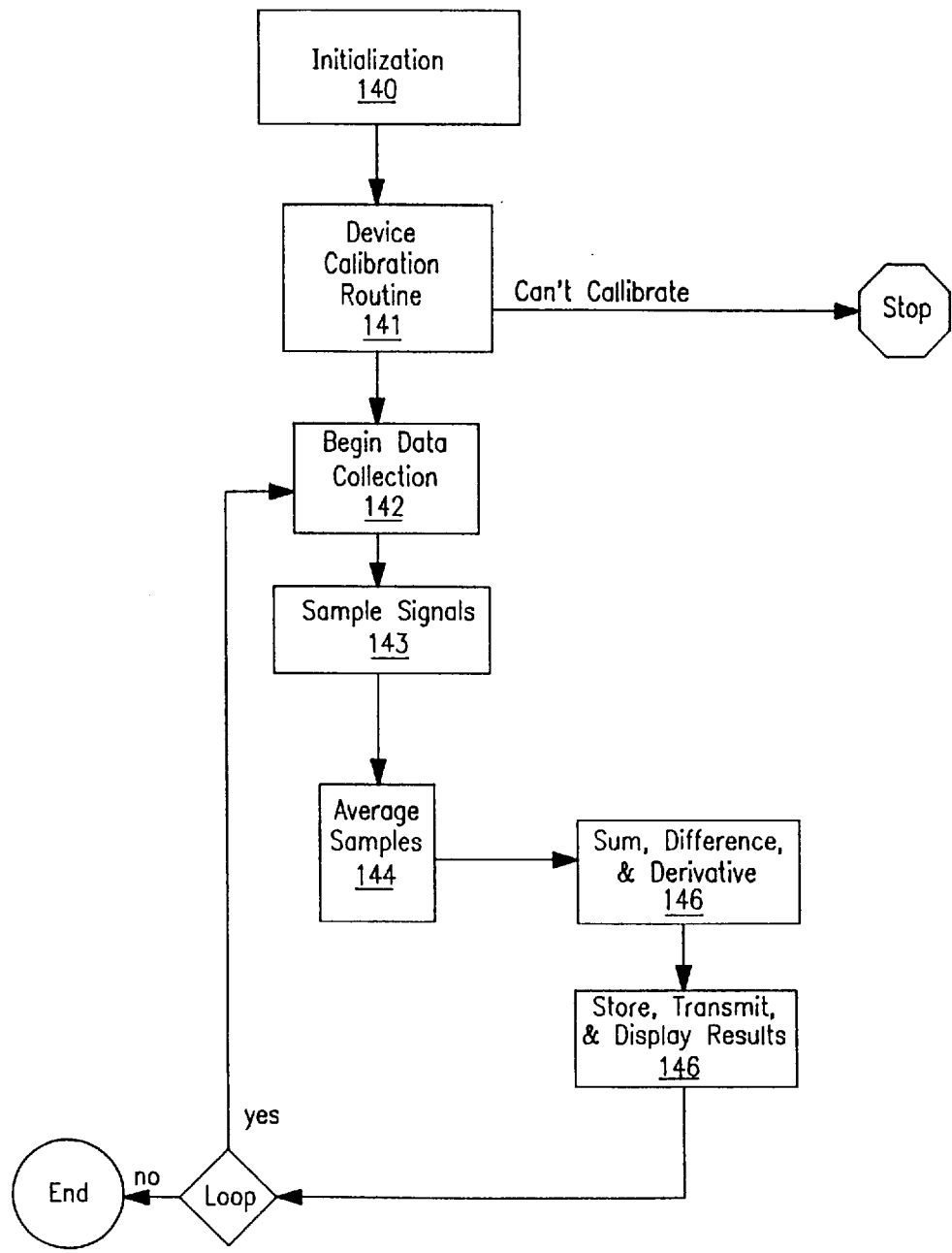
FIG. 12 is a software flow diagram of the software used with the circuitry of FIG. 11.

FIG. 12 shows the software. Initialization of the system 140 takes place whereby the analog and digital system is set up and configured properly. The digital memory, communication and telemetry are configured as in FIG. 11. Secondly the device calibration takes place such that the gain of the amplifiers is set electronically by software. The gain of the amplifiers is set to an acceptable range so that digitization can take place accurately, as well as other small internal routines to determine whether the derivative is working properly or not. In the case that the calibration cannot take place, the program will stop and alarm the user. The alarm 134 represents "not working properly, please reset", etc. After calibration is completed successfully, data collection is begun. Data collection is taken in a loop format starting with 142. It starts with turning the lamp on, and sampling the signal, 143. Approximately 500 points of data are taken in rapid succession over approximately ½ second sampling interval or less. That data is accumulated, then the lamp is turned off after a delay period, which is set by the user and by the software. The samples are collected and then averaged at 144. This average is then used at 145 to calculate the sum, difference and derivative. In this case the calculated derivative serves as a redundant comparison with the analog derivative calculated in 125 of FIG. 11. In addition to the averaging of 760 and 850 nm, the derivative signal is also averaged and sampled in the same way, for example with 500 points. By this means a calculated derivative as well as a sample derivative are obtained which are compared to provide a much more repeatable and reliable result for an alarm.

The data after it has been manipulated in 145 will be stored, appropriately transmitted and/or displayed. In addition the alarm is set off if necessary at this point. Then finally an independent timer or delay would be introduced. The processor is delayed for a set period to obtain desired lampflash/data collections frequency.

The sequence is thus: lamp on, collect sample data, lamp off, collect noise data, average sample, calculate sum, difference and derivative, then transmit, display etc., wait if necessary, and then turn on the lamp again and repeat the whole procedure.

Referring to FIG. 11, dark current/noise correction in this analog system is accomplished by sequencing the data collection using the microcontroller. The data is collected in two sequencing steps. One step has light on and the other step has light off. The data collected with the light off represents the dark current. The data collected in the first and in the second cycle are digitally subtracted in order to obtain intensity data corrected for the dark current noise.

Figure 13:
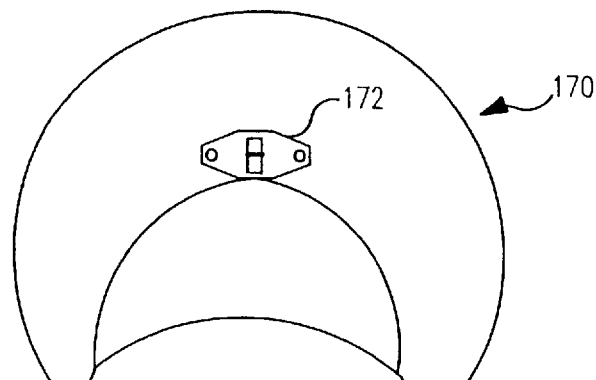
FIG. 13 is a front of a helmet according to the invention.

Referring now to FIG. 13, a helmet 170 is shown having a tissue oximeter 172 molded at a position to snugly engage the head of the wearer when the helmet is put on, typically at a position free of body hair, e.g., at the forehead above the eyebrow. The oximeter is of the type, e.g., as described in FIG. 8b, having a source for transmitting NIR light, a detector to receive the light scattered from tissue such as brain tissue and a barrier to engage the head between the light source and the detector to prevent light traveling laterally between source and detector through subcutaneous layers. Preferably, the oximeter in the helmet includes a control circuitry on a miniature chip and preferably circuitry and/or software are provided for determining the rate of change of oximetry readings and for comparing the rate of change to a standard.

Figure 14A:
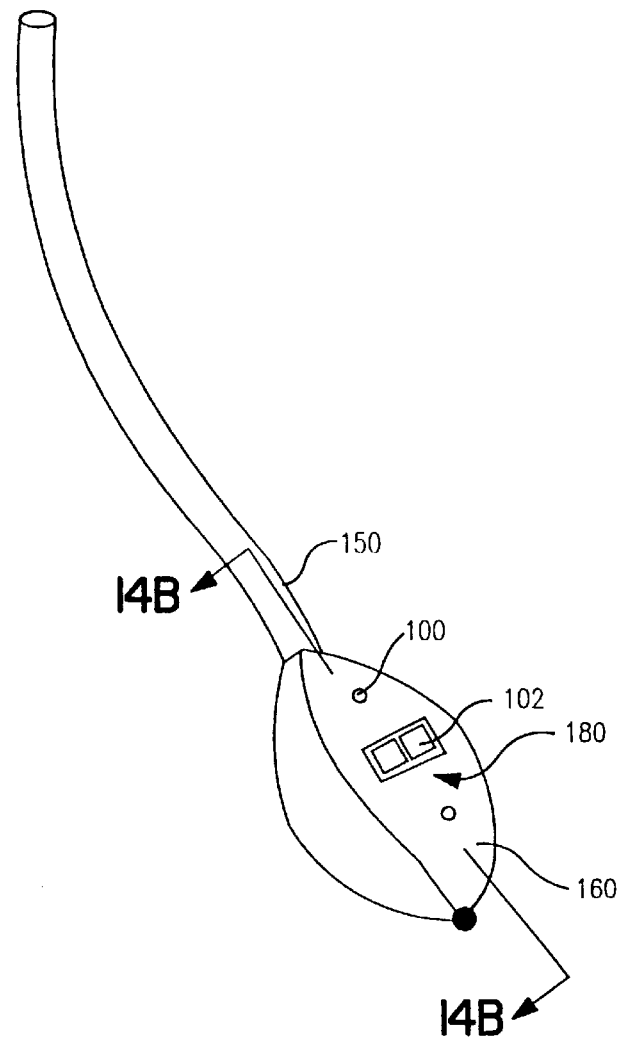
FIGS. 14A and 14B show an endoscopic oximeter according to the invention.
Figure 14B:
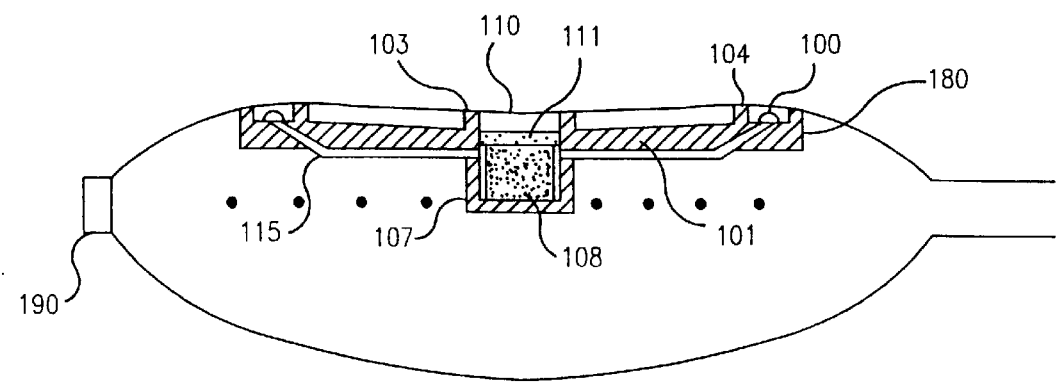

Referring now to FIGS. 14a–14b, an oximeter 180 is disposed on a catheter 150 (e.g., an endoscopic catheter), having an inflatable balloon 160 and endoscope optics 190. The oximeter 180 is preferably of the design illustrated in FIG. 7, and is molded or otherwise attached to the outer surface of the balloon. Controlling and detected signals may be passed to and received from the oximeter by wires passing through the balloon and a lumen within the catheter or by transmission from the oximeter to a receiver outside the body by telemetry as discussed, e.g., with respect to FIG. 9. In operation, the catheter, with the balloon deflated, is passed through a body lumen to the position of interest, guided for example, by fluorimetry or by endoscopic viewing. The balloon is then inflated to press the oximeter against the tissue of interest and measurements taken as described above. The technique and apparatus may be applied, for example, to body lumens such as the GI tract (e.g., for measurements of GI track wall ischemia or hypoxia as determined to be a preliminary indicator of multiple organ failure) or to blood vessels, employing an angiographic catheter for analysis and treatment of occlusions, etc. Still other embodiments are possible. For example, a "postage stamp" oximeter may be provided, e.g., for emergency use (self-contained system with alarm as discussed), where the oximeter is held to the subject by an adhesive pad, positioned peripherally around the device. Another embodiment includes providing a water impermeable coating about the device for applications in the presence of water, e.g., for scuba divers, etc. In yet another embodiment a phase modulation spectrophotometer may be employed for calibration of the oximeters described above, especially for in-home or long-term portable monitoring applications, e.g., greater than 3 hours. Such calibration allows more quantitive measure of blood oxygen levels, etc. One example of such a spectrophotometer can be found in U.S. Pat. No. 4,972,331, the entire contents of which is hereby incorporated by reference. It will also be understood that implantable probes may be configured using direct wiring, with corresponding punctures in the skin as an alternative to telemetry.

Figure 15:
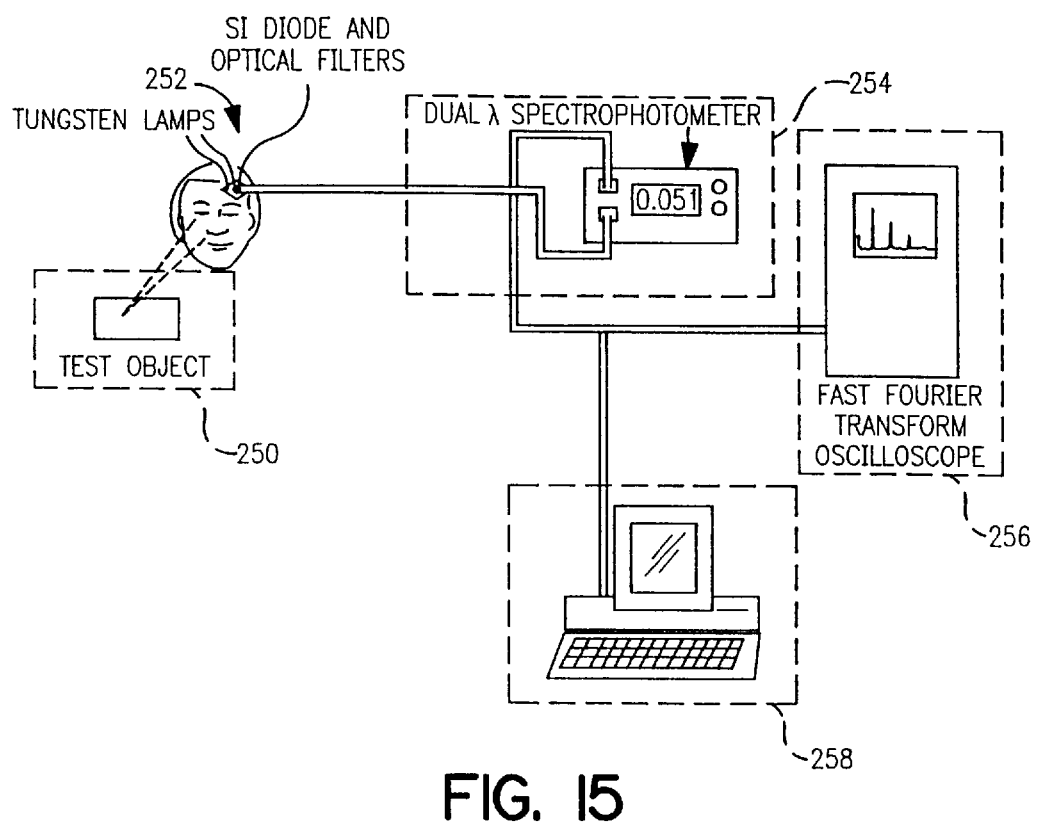
FIG. 15 is a block diagram of a low frequency cognition spectrophotometer.

Another preferred embodiment of the present invention is a cognition spectrophotometer system, shown diagrammatically in FIG. 15. The cognition spectrophotometer examines the relationship between brain activity, oxygen delivery, oxidative metabolism, and blood flow by employing photon migration from a source placed on the surface of the head through the skin, skull and underlying brain tissues to a detector also located on the surface of the head. As already discussed, light is absorbed and scattered along the migration path.

Referring to FIG. 15, the system comprises the following five modules: a stimulation module 250, a sensor module 252, a control circuit module 254, an analyzer/display module 256, and a computer/printer module 258. Stimulation module 250 is used to stimulate a specific brain function through a visual, acoustic, sensorimotor, or other stimulation. Sensor module 252 is connected to control circuit module 254; preferred embodiments are shown in FIGS. 5 through 13, 22, and 23. FIGS. 10 and 11 diagrammatically show the sensor, control circuit, display and computer/printer modules. The display module of FIG. 15 is a fast Fourier transform oscilloscope. The operation of sensor module 252 is governed by control circuit module 254 which controls the radiation emission and detection, collects the data, and sends the data to analyzer/display module 256 and to computer/printer module 258. The operation of the whole cognition system is controlled by a computer of computer/printer module 258.

The cognition spectrophotometer system, in one embodiment, measures the low frequency and power spectra of fluctuations of absorbances attributed to the blood concentration changes in the frontal region of the brain. The low frequency recurrences of brain activity are linked to blood concentration increases and are detected in human subjects with an optical device. The spectrophotometer employs wavelengths of light sensitive to oxygenation/deoxygenation of hemoglobin in the red region of the spectrum, i.e., absorbency changes at 760 nm are balanced against those at 850 nm in equal proportions. The difference in the absorbency changes is highly sensitive to the oxygenation/deoxygenation of hemoglobin ($HbO_2$/Hb) and is insensitive to the changes of blood concentration. The sum of the absorbency changes of these two wavelengths is sensitive to the blood concentration changes and insensitive the hemoglobin to oxygenation/deoxygenation of hemoglobin changes (approximately one-half of the 760 nm signal is added to the 850 nm signal). The data reported in FIGS. 16–21 have been obtained in the sum mode and the time dependence of changes of blood concentration has been measured. An alternative method to the sum of two wavelengths is to use a single wavelength apparatus, shown in FIGS. 22 and 23, for example, 800 nm which is an isosbestic point in the Hb/$HbO_2$ spectrum. Other wavelengths can be also used, for example, 950 nm which is sensitive to water absorption, or wavelengths sensitive to endogenous or exogenous pigments.

The cognition spectrophotometer of FIG. 15 was tested on several human subjects who were juniors or seniors from Central and Girls High Schools in West Philadelphia. The subjects were exposed to visual stimulation by a series of abstractions composed of analogies taken from SAT examinations. (All studies were conducted under IRB-approved protocol #M1025 for acquiring optical signals from the forehead of human subjects at rest and under test. Parental approval was obtained for those subjects under 18 years of age.) Sixty of these abstractions were displayed for an intended time of 11 minutes corresponding to 16 iterations of the Fourier transform oscilloscope 256 of the display module (FIG. 15). The advance of one analogy to the next was dictated by the subject's conclusion that the analogy has been understood. The analogies presented to the subjects in this study were intended to simulate associative responses. The analogies continued within the 11-minute interval as long as the subject felt that he/she was adequately able to concentrate on them. If the subject's attention was diminished due to fatigue, etc., the test was terminated. Usually more than 11 out of the 16 iterations of the Fourier transformations were obtained and often the full 16 were obtained. At this point the subject was told to "rest".

Figure 20A:
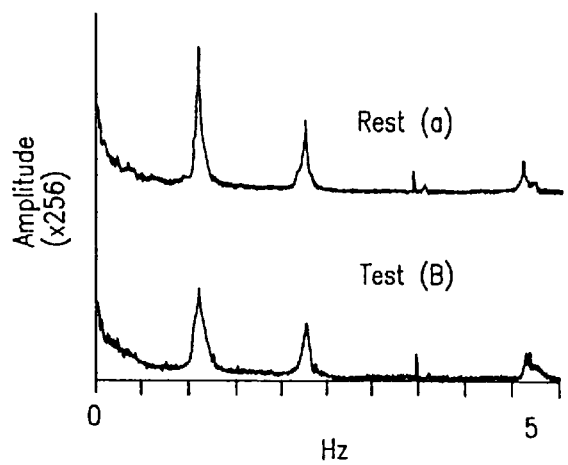
FIGS. 20a and 20b show frequency analyses of optical signals of subject U at rest obtained by the cognition spectrophotometer of FIG. 15.
Figure 20B:
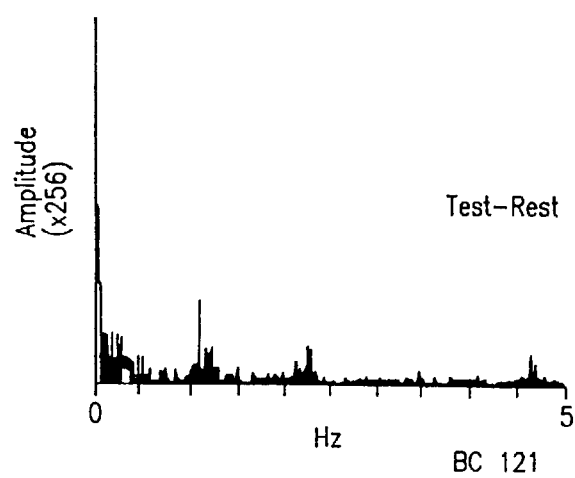

No analogies were presented during the "rest" intervals. The Fourier transformations of the optical data for two successive 11-minute intervals were recorded and subtracted and were entitled "rest"-"rest" (FIG. 20).

The sensor module used in this study consisted of two tungsten flashlight bulbs placed 4 cm each from the two silicon diodes (4 mm×10 mm), each equipped with an interference filter transmitting a 10 nm wide band centered at 760 nm and 850 nm. Thus, this system provided two photon migration paths with input-output separation of 4 cm. A preamplifier coupled the optical signals to an amplifier unit that took the sum and difference of the signals suitably corrected as described above. The tungsten lamps were pulsed at 3 Hz so that absorbance measurements were time shared with background measurements and the one was subtracted from the other to provide background light correction via sample and hold techniques for the difference circuit.

Figure 16:
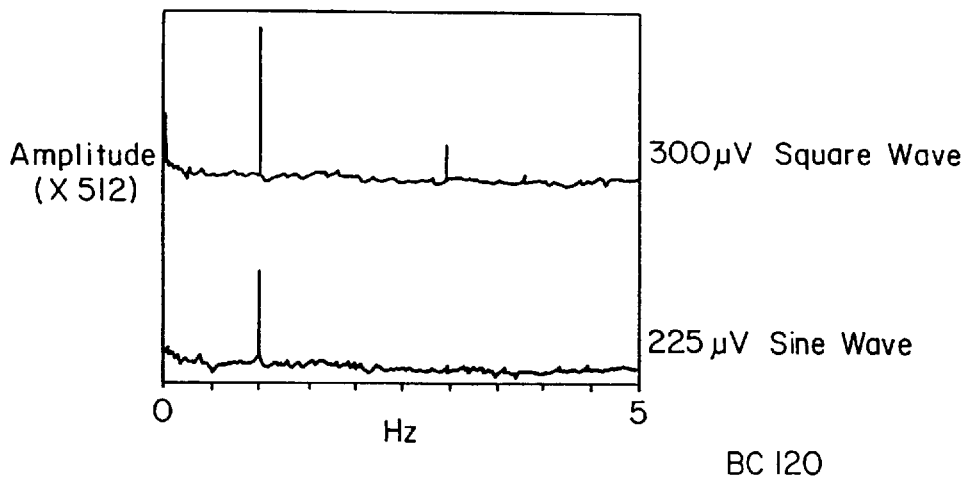
FIG. 16 illustrates the response of the Fourier transform oscilloscope of the cognition spectrophotometer, shown in FIG. 15, to 300 $\mu$V peak-to-peak square wave (top trace) and 225 $\mu$V sine wave (lower trace)
Figure 17:
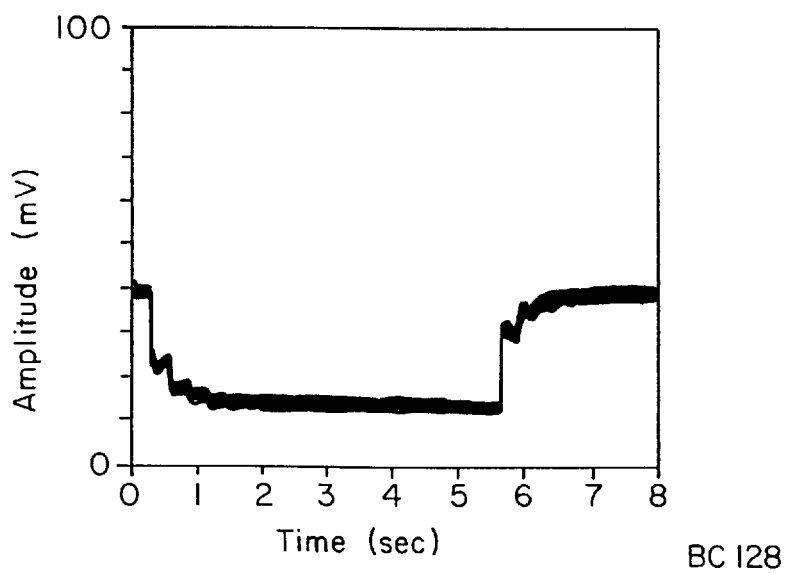
FIG. 17 illustrates the response of the DC amplifier to a square wave.

In a response speed test, the output of the filtered sum response reached 70% in 1 sec, as shown in FIG. 17. The output signal was directly connected to the Fast Fourier transformer Tupe 440 (Nicolet) which was used in the DC-coupled mode on the 200 millivolts scale. The conditions were set for 16 iterations in the 0–5 Hz scale for a total interval of data acquisition of 10 min. The recording sensitivity was 220 $\mu$v/cm at ×512 gain (FIG. 16) and 440 $\mu$v/cm at ×256 gain. The noise level of FIGS. 16–20 was about 20 mV. The total signal was 115 mv and the noise level was 0.2%. The full scale sensitivity was 1.0% of absorbance change at ×512 and 2.0% at ×256. FIG. 16 illustrates the response of the Fourier transform oscilloscope to 300 $\mu$V peak-to-peak square wave (top trace) and 225 $\mu$V sine wave (lower trace), wherein 16 iterations at ×512 gain were used.

Referring to FIG. 17, the response of the DC amplifier to a square wave reaches 70% in 1 sec. Thus, the system is responsive only to frequency components in the 0–3 Hz region and records the recurrence of these components. Static experiments carried out simultaneously indicate that the sum of the peaks of the test trace corresponds to an increase of blood concentration of approximately 5% of the total signal.

The ideal study control would repeat every feature of the study except the specific changes due to recognition of the analogies given to the subjects. Thus, the study was repeated with two intervals of "rest" of duration equal to that of the "rest"-"test" study. The "test"-"test" was not considered appropriate because the double duration of the "test" might have led to accommodation in the responses, and because the response to different "tests" could be different. This study had the sensor module placed in one location during the test interval; however, mapping of the "test" response by locating the sensor module in different locations on the exterior of the head is feasible.

Each recurrent signal is indicated by a peak at a particular frequency (Hz) in the illustrations. Peaks present in the "rest" recording are usually related to arterial pulse and related frequencies. Additional frequencies are usually observed in the "test" interval, and the Fournier transforms are readily subtracted by the instrument ("test"-"rest"). Some recurrent frequencies may also contribute to the increasing intensity of the spectra in the low frequency region. Peak size, as well as the 1/f noise is increasing as the frequency decreases.

Both the "test" and "rest" signals contain a signal of the arterial pulse of the brain tissue. At "rest" and "test", signals at 1–2 Hz and related harmonics are often observed. At "rest", a low frequency component is detected at various locations on the forehead and tracks closely the frequency of arterial pulse as detected on the wrist. However, these signals nearly completely cancel in the "rest"-"rest" difference Fourier and are thus attributed to the arterial pulse in the brain tissue. Occasionally, the "test"-"rest" shows a difference signal due to altered arterial pulse rate during the "test".

Figure 18A:
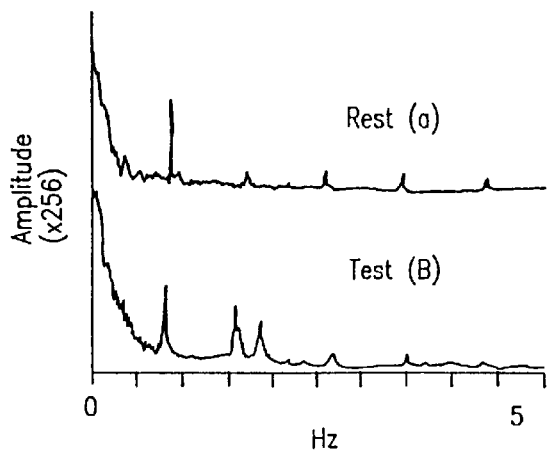
FIGS. 18a and 18b show frequency analyses of optical signals of subject U obtained by the cognition spectrophotometer of FIG. 15.
Figure 18B:
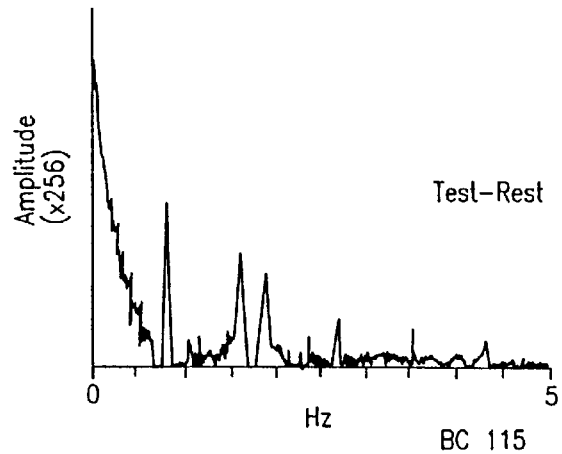
Figure 19A:
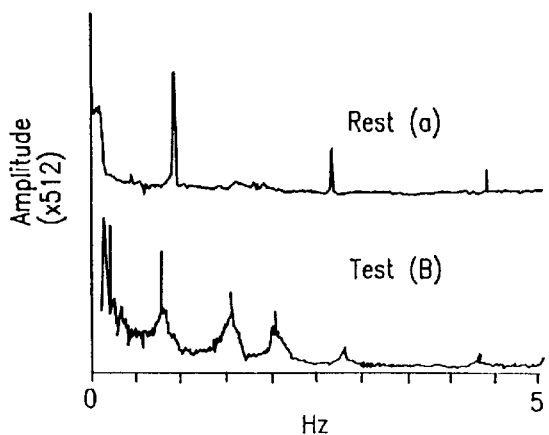
FIGS. 19a and 19b show frequency analyses of optical signals of subject B obtained by the cognition spectrophotometer of FIG. 15.
Figure 19B:
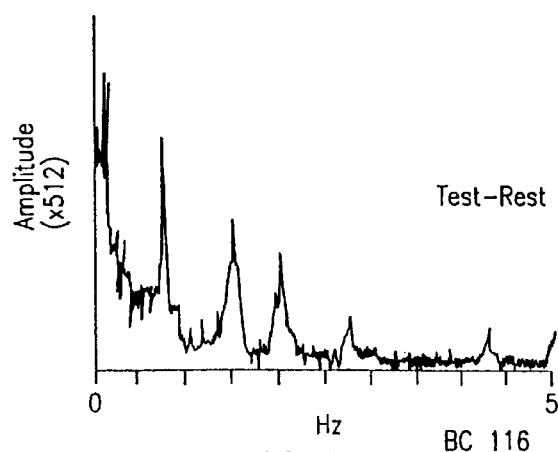

Referring to FIGS. 18 and 19, the Fourier transform spectrum of the "test" interval and the "rest" interval of a female subject (U) are displayed as traces b and a, respectively. 16 out of the 16 scans were obtained (study 24, Table I). The frequency-scale is 0–5 Hz, the amplitude scale represents a gain of ×256. The subject's heart rate was 81 BPM (1.3 Hz). However, in the "rest" spectrum, the predominant peak is at 0.8 Hz, approximately 2% of the total signal. Small, sharp peaks appear at 1.7, 2.7, 3.5 and 4.7 Hz. Similar peaks of similar amplitude appear in the "test" study and are thus not "activity related". However, new large peaks appear at 1.6 and 1.8 Hz in the test spectrum.

The difference of the two Fourier transforms designated "test"-"rest" shows a recurrence of signals at particular frequencies associated with presentation of analogies. There is a preponderance of the 0.8, 1.6 and 1.8 Hz peaks and a small contribution of a 2.8 Hz peak. The largest peak corresponds to 1% of the total signal. Of interest from the theoretical standpoint is a large component of 1/f noise in the "test"-"rest" diagram suggesting that recurrence at the very low frequencies is less probable than at the higher frequencies. In a repetition of this study (#25), a 2.3 Hz peak was observed (see Table I) and the doublet peaks at 1.7 and 1.9 Hz were again observed in "test"-"rest".

Another frequency spectrum of a female subject (B) is shown in FIG. 19 where the rest spectrum shows a strong peak at 0.8 Hz, presumably due to the heart rate, and a second peak at 2.7 Hz. After 7 iterations, the subject spontaneously ceased the study. The Fourier transform of the "test"-"rest" spectrum contains broad peaks at 0.8, 1.5, 2.0, 2.7 and a peak at 4.3 Hz. The largest peaks exceed 1% of the total signal. The 1/F noise observed in the spectra appears to contain an unresolved peak at 0.2 Hz.

Referring to FIG. 20, frequency analysis of two "rest" spectra of a subject U shows somewhat stronger peaks than in the "rest" study of FIG. 18 at 1.2 and 2.3 Hz with a small peak at 4.6 Hz. In the "rest"-"rest" traces, only small broad peaks are observed. There are small differences that are attributed to variations in the arterial pulse and its higher frequency components of amplitude and frequency that differ in the first "test" as compared to the second. This is confirmed in Tests 27 and 28. In no case was a new distinctive peak observed as in "test"-"rest" studies. Table I summarizes 31 tests of 9 individuals (6 females, 3 males) over a six-week period. Column F lists the frequencies observed at "rest", Column G, the frequencies during the "test" interval (except Cases 8, 27, 28). Column H gives the recurrence of frequencies appearing in the substraction of "test" and "rest" in the Fourier transform. A high consistency is indicated by our observation of recurring frequencies in 24 out of 28 tests (85%) (all but four tests 2, 3, 9, and 24). In No. 24, increased 1/f noise was observed (Column H). Tests 8, 27, 28 were controls in which "rest"-"rest" intervals were subtracted.

Figure 21:
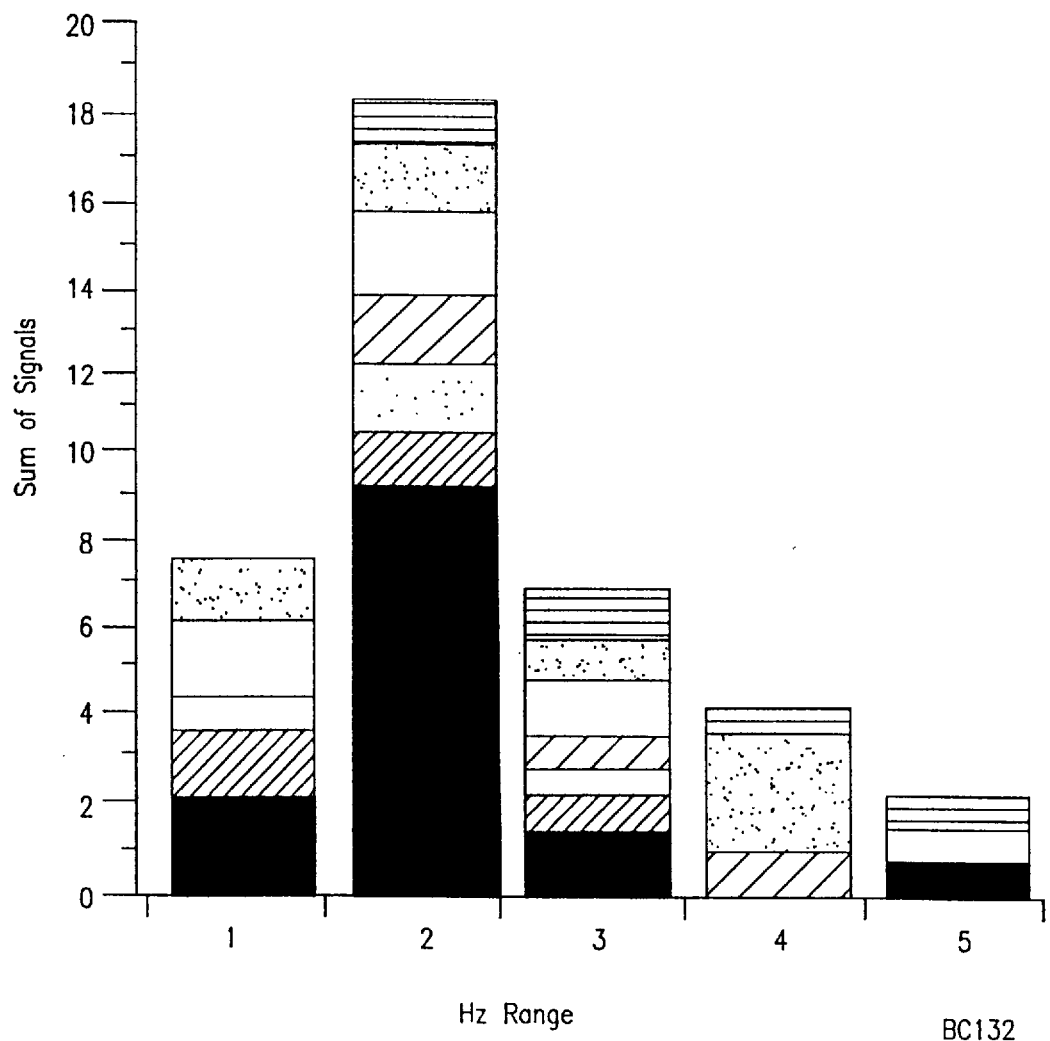
FIG. 21 shows a histogram display of the distribution of frequencies obtained by the cognition spectrophotometer of FIG. 15.

Referring to FIG. 21, the histogram displays the recurrence of frequencies in the range 0–4 Hz taken from Column H of Table I. Each individuals frequencies are cross hatched. There appears to be a preponderance of 1–2 Hz signals taking into account that the frequency range is limited by commingling with 1/f noise at the low end, and the frequency response of the instrument diminishes signals above 2.5 Hz.

Figure 21A:
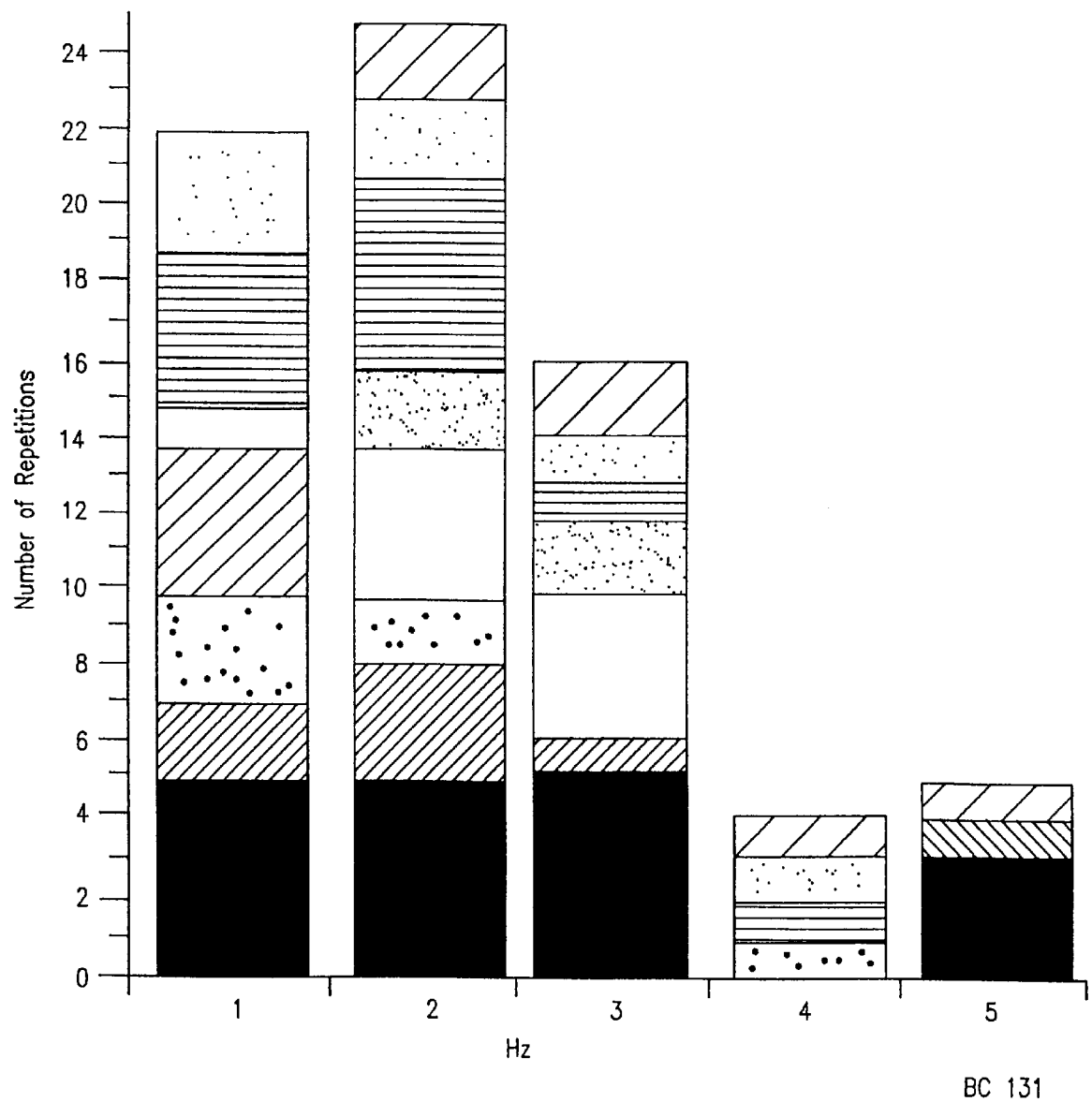
FIG. 21a shows a histogram display of the distribution of energy (area) in the peaks obtained by the cognition spectrophotometer of FIG. 15.

The intensity value at the particular frequency gives the power spectrum of FIG. 21a for 1 Hz intervals. The largest peak is at 1.5–2.5 Hz. In both cases, the stippling of the chart identifies the nine subjects.

A more detailed plot of the data of Table I, including those that exhibited three or more frequencies, indicated that this ensemble exhibited equal-maxima at the harmonic frequencies 0.8 and 1.6 Hz and approximately equal peaks at 1.2, 2.6 and 4.2 Hz respectively, a rough approximation to harmonics of frequencies of 0.08 and 1.2 Hz. However, there was no peak at 3.0, 2.1 Hz at the exact harmonic frequencies.

The cognition spectrophotometer system, used in this trial, utilizes only the sum of the 760 nm and 850 nm signals. The isosbestic point in the $Hb/HbO_2$ spectrum is approximately at 800 nm, and thus the balanced sum of $Hb/HbO_2$ absorbances at 760 and 850 nm measures the blood concentration. $Hb/HbO_2$ is the principal absorber at these wavelengths since the signal is over 20 times that of cytochrome $aa_3$. The fact that no significant results were obtained in the difference recording suggests that the oxygenation/deoxygenation of the frontal lobe tissue was not a predominant effect in these studies. Changes of light scattering are not separated from absorbance changes when using continuous light, and would be expected to uniformly affect both 760 and 850 nm.

Furthermore, results of the present trial are compatible with other studies using PET, SPEC, and MRI which also suggest existence of blood flow changes during brain stimulation and the fact that the arterial pulse is the strongest signal in both "rest" and "test"; this supports the interpretation attributing the measured signal to blood concentration changes.

It is expected that the metabolic activities induced by brain stimulation contain low frequency component signals. The cognition spectrophotometer system of FIG. 15 records repetitive fluctuations in the optical signal in a 10 min stimulus interval. Thus, the employed method requires not only a blood concentration increase during stimulation, but also periodic repetition of the increase within the tissue volume optically sampled. Such increases need not be repeated at identical locations but may have a spatiotemporal distribution. A 4 cm separation of input/output gives a mean penetration of 2 cm and a tissue volume of roughly 5 ml within which the repetitive response is observed.

Figure 22:
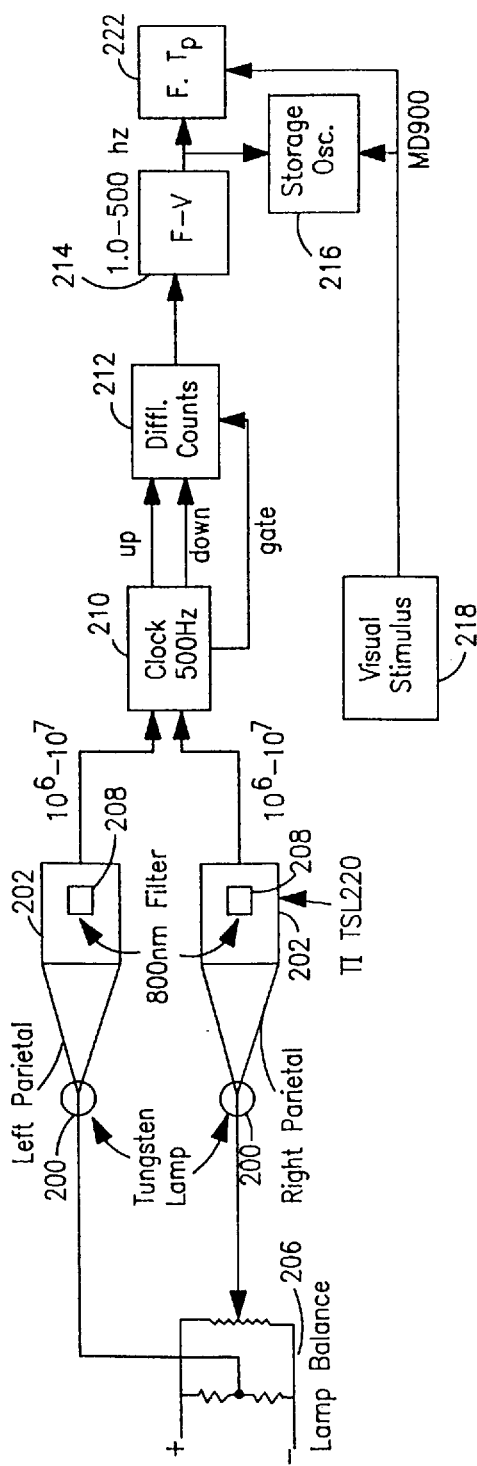
FIG. 22 is a block diagram of a fast lateralization detector of the cognition spectrophotometer of FIG. 15.

Our narrow band width and relatively short iteration time (<11 min.) in this trial was set by the characteristics of an available instrument, and the detected spectrum may be only a portion of the total frequency spectrum. As shown in FIG. 22, a much faster instrument can be also used. The limits to the bandwidth of optical studies are set both by signal-to-noise and by the intrinsic relaxation time of photon migration in the brain.

In the above described trial only a crude localization of the response was employed by placement of the input and output ports. The optical system was designed to respond optimally to blood concentration changes (in a volume of about 3-5 ml) in the frontal/temporal cortex, and the analogies were designed to stimulate activity in the frontal region. When left and right sides of the forehead were compared, the success rate of new peaks in the Fourier transform was two times greater in the left side.

An important aspect of future development of the optical methods is the rate at which data may be accumulated. The travel time of photon migration over a path length of one meter is 23 ns with a 4 cm input/output separation. The signal to noise ratio will determine the number of iterations of the test, which in these preliminary studies, was approximately 50 over a period of 11 minutes.

The photon migration kinetics are responsive to both light scattering and light absorption. Whilst absorption has been stressed in these studies, light scattering is much closer to the primary events of neuronal/axonal response than to the blood flow/blood concentration change, both in anatomy and in time.

In this trial, the low frequency recurrence of changes of blood concentration was measured in portions of the brain that are approximately 2 cm deep from the surface of the skull of the subjects. Application to other stimuli (for example, visual, acoustic, sensorimotor) that affect function in other regions of the brain may be possible. (Visual stimulation registered in the visual cortex was not used in the present trial because dense hair covered the surface of the back of the head in the population studied.) It is expected that the recurrence frequencies which are observed in the cognitive tests would be significantly diminished in cases of neuronal deterioration. Thus, the cognition spectrophotometer system enables simple non-invasive and rapid testing of cognitive function of different regions of the brain.

The cognition spectrophotometer system is designed to provide objective evaluation of functional activity of the brain with a simple and inexpensive device. The system enables a wide range of studies of the brain activity in responding to appropriate tasks and presents an alternative to several expensive techniques (for example, MEG and EEG) or ones that involve radioactive techniques. Thus, screening for neuronal deterioration and/or deterioration of brain function can be done conveniently and continuously.

Figure 23:
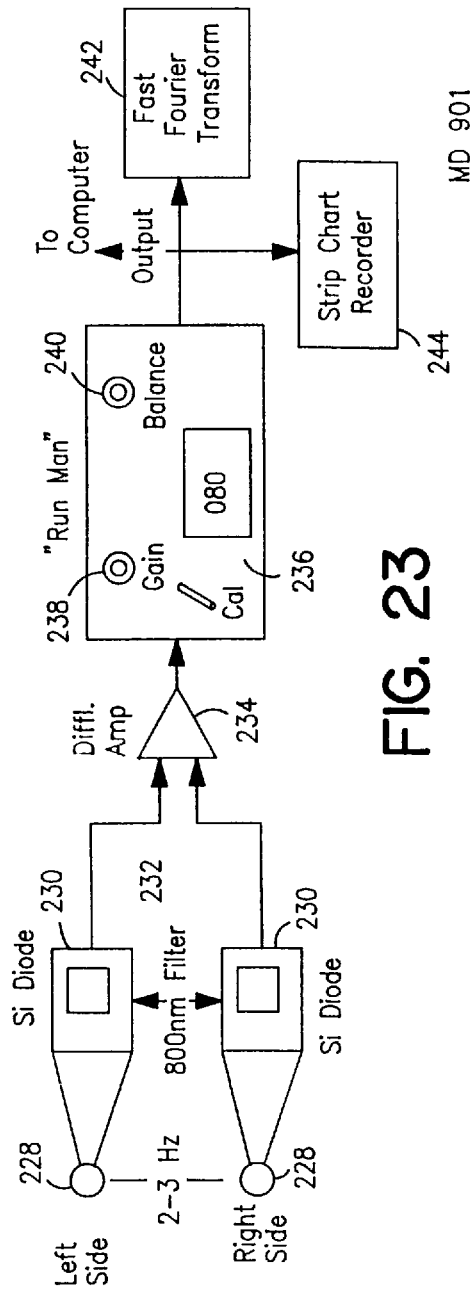
FIG. 23 is a block diagram of a low frequency lateralization detector of the cognition spectrophotometer of FIG. 15.

In another embodiment, shown in FIGS. 22 and 23, the cognition spectrophotometer simultaneously records lateralized potential difference of two brain hemispheres. It has been suggested that lateralized readiness potential can measure electrical brain activity that is related to preparation of movement. This measure has been used to illuminate presetting processes that prepare the motor system of the brain for action. The lateralized potential also demonstrates the presence of transmission of partial information in the cognitive system and identifies processes responsible for the inhibition of responses.

The cognition spectrophotometer, shown in FIGS. 22 and 23, measures the lateralized difference potential optically by measuring increased blood concentration in localized regions of the brain that are activated by the lateralized readiness potential. The spectrophotometer simultaneously records and compares optical signals from both hemispheres. The detected data are subtracted in real time, the difference signal is recorded as an analog signal via an A/D converter and a computer manipulates the data and takes the Fourier transform of the data. The lateralized difference potential is measured as blood concentration changes using 800 nm light; however, light of other wavelengths sensitive to other constituents of the brain tissue can be used.

For high frequency measurements, the cognition spectrophotometer can use a fast lateralization detector, shown in FIG. 22. The detector has two tungsten light sources 200 placed on the left and right parietal bones and two light-to-frequency converters 202 placed also on the parietal bones at a distance of 4 centimeters from the sources. The intensity of each lamp 200 is regulated differentially by a lamp balance 206 in order to achieve the same light intensity output from the two light sources. An 800 nm interference filter 208 is placed on each silicon detector 202. The silicon light-to-frequency converters are adjusted by the frequency light intensity control to output the same frequency in the range of $10^6$ to $10^7$ Hz.

The fast lateralization detector measures a frequency difference between the two silicon detector converters 204. The signal of each detector is routed to a differential counter 212 using a 50 Hz clock 210. If the differential count is zero, both detectors are outputting the same frequency signal. If there is a difference in the signals detected at the two detectors, the differential count is not zero. The differential signal is processed by a frequency-to-voltage converter 214. Converter 214 operates in a low frequency range and detects frequency differences. The voltage output is Fourier transformed, stored and apalyzed in view of a visual stimulus 218 or other brain activity stimulus.

Referring to FIG. 23, in another preferred embodiment the cognition spectrophotometer utilizes a narrow band lateralization detector which is sensitive to the low frequency changes. Tungsten lamps 228 placed on the parietal bone are flashed at frequencies on the order of 2 to 3 Hz in order to provide for correction of the dark current. Each detector 230 has an 800 nm interference filter 232. A differential amplifier 234 is used to measure difference in the light intensity arriving at the two detectors. The output of the differential amplifier is coupled to the "RunMan" control unit, a modified version of the control unit shown in FIGS. 10 and 11. Balance 240 is set so that the two signals are balanced at zero millivolts. The output signal is connected to the fast Fourier transformer 242, recorded on the strip chart recorder 244 or send to a computer. The lateralization detector of FIG. 23 measures differential low frequency fluctuations of absorbances attributed to the brain blood concentration changes in different respective regions of the two brain hemispheres. The localization of the radiation to the appropriate region of the brain hemisphere is achieved by selecting proper location and separation of the input and output ports of the source-detector pair (FIGS. 15, 22, 23 and 24). For example, as described above, 4 cm separation of the source and detector on the exterior of the head gives a penetration of about 2 cm of the banana-shaped migration path of the radiation.

Figure 24:
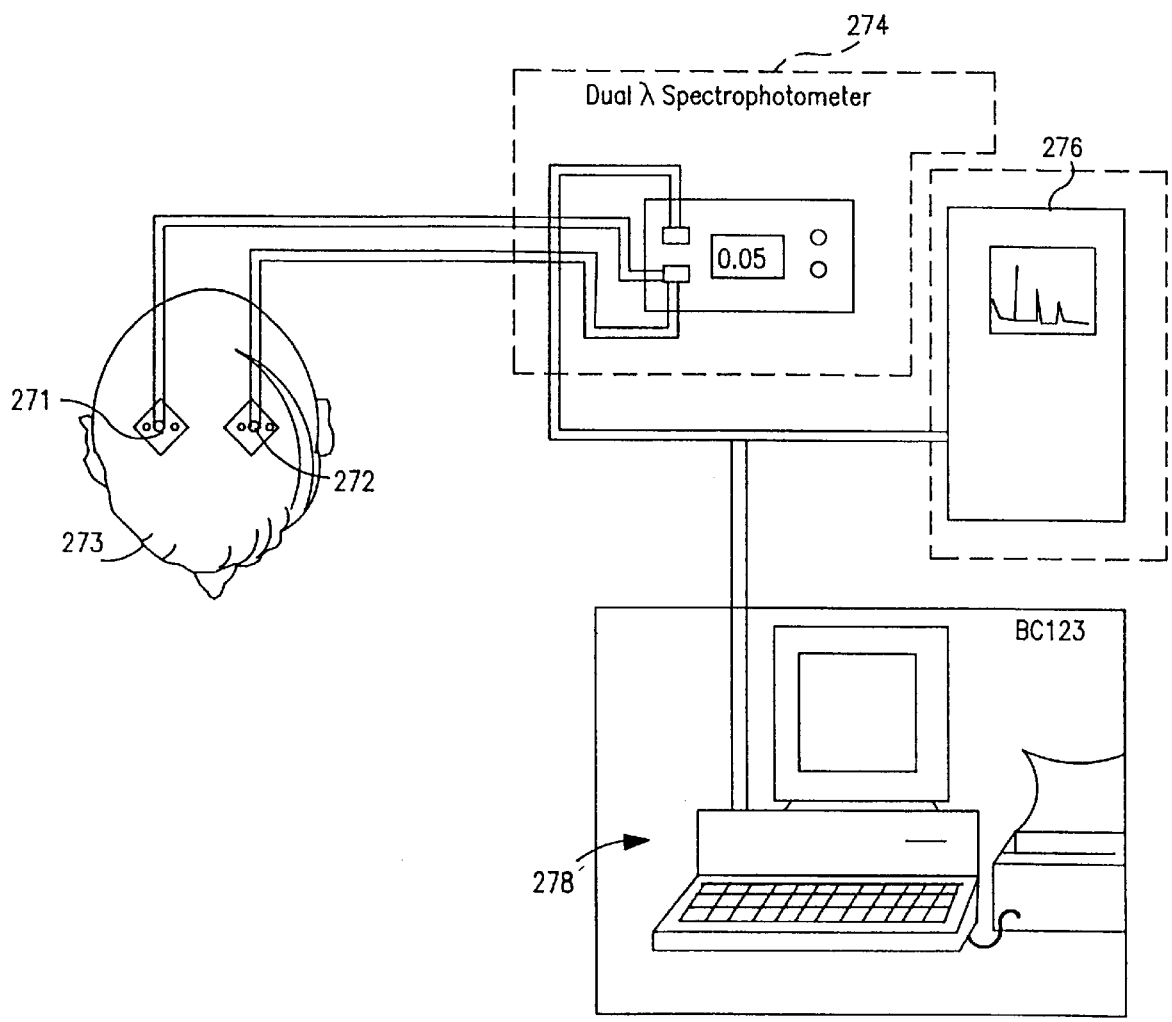
FIG. 24 shows a differential spectrophotometer system.

Referring to FIG. 24, another preferred embodiment of the present invention is a differential spectrophotometer system for in vivo examination of a tissue of a human by measuring changes in electromagnetic radiation migrated in a path of two localized tissues of interest. The first tissue of interest, used to collect reference data, is expected to have normal physiological properties. The second tissue of interest is a tissue expected to have regions of pathological or pathophysiological changes, for example, a tumor or bleeding. An approximate localization of the tissue of interest having pathological or pathophysiological changes can be determined by diagnostic assessment of the subject, for example, by a neurologic examination, evaluation of the symptoms, etc. In absence of any pathophysiological changes both the first and second localized tissues of interest (for example, regions of the left and right hemisphere of the brain, left and right breast, or left and right arm) are expected to produce nearly identical signals of photon migration. On the other hand, if a region of an organ, for example, the right hemisphere of the brain, has a tissue of abnormal pathophysiological state, the tissue is expected to produce a signal which differs from the signal of the normal tissue of the left hemisphere; thus, the differential signal will be non zero.

Referring to FIG. 24, the differential spectrophotometer system comprises the following five modules: two sensor modules 271 and 272, a control circuit module 274, an analyzerldisplay module 276, and a computer/printer module 278. Each of the two sensor modules 271 and 272, placed on the subject's head 273, comprises at least one source and detector as shown in FIGS. 5 to 8c, 22, 23. The operation of each sensor module is governed by control circuit module 274 which controls the radiation emission and detection, collects the data and sends the data to analyzer/display module 276 and to computer/printer 278. The operation of the whole cognition system is controlled by a computer of computer/printer module 278.

The differential spectrophotometer introduces electromagnetic radiation of at least one selected wavelength (for example, 800 nm) into the brain simultaneously at a first and second input port of the 271 and 272 sensor modules. Both the first input port and the second input port are placed at a first selected location and a second selected location on the exterior of the head, respectively. Two detectors, placed at a first and second location on the exterior of the head, are simultaneously detecting radiation that migrated along the banana-shaped paths in the two brain hemispheres from the first and second input ports to the first and second output ports, respectively. Control module 274 collects the detector signals, corrects for the noise signals and sends the corrected signals to analyzer/display module 276 and to computer/printer module 278. Control module 274 can also create a differential signal, as described in FIGS. 22 and 23.

The system processes the signals of the two detectors and evaluates the processed data to determine whether the radiation migrated in a tissue of abnormal physiological or pathophysiological properties.

In another application, the differential spectrophotometer system can be used to determine physiological or pathophysiological properties of a breast tissue. Here, one sensor is placed on one breast and the other sensor on the other breast. Similarly as for the brain, breast tissue is examined by comparing the two signals of the radiation that migrated in the two paths in the respective breast.

The lateralized detection technique that simultaneously measures photon migration in two migration paths (FIGS. 22, 23, and 24) achieves better signal-to-noise ratio than the technique which detects signals from only one migration path (FIG. 15). Some lateralized events involve only blood volume changes or only blood concentration changes; thus, the system can probe the tissue using radiation of only one selected wavelength. Other lateralized events may result in oxygenation/deoxygenation changes; thus, the system uses radiation of at least two wavelength (for example, 760 nm and 850 nm) coupled into an organ alternatively. In this case, each sensor comprises either one source-detector pair adapted to operate at at least two selected wavelengths, or two wavelength specific source-detector pairs. Signals of each wavelength obtained from the two sensors are again differentially manipulated to determine desired tissue properties. As described above, the localization of the radiation is controlled by placement and position of each source and detector.

One of ordinary skill in the art will appreciate that the present invention is not limited to the particular embodiments described in detail. Modifications to the circuitry disclosed, and other aspects of the spectrophotometer configurations disclosed, as well as other modifications to the physical arrangement of the present apparatus will be obvious to those of ordinary skill. Further, the present invention is not limited to any of the uses described herein. In order to fully appreciate the scope of the present invention, reference should be made to the following claims.

What is claimed is:

1. A method of transcranial examination of biological tissue by measuring changes in electromagnetic radiation scattered and absorbed in migration paths in the brain, comprising providing a first light source and a second light source optically connected to a first input port and a second input port positioned on the exterior of the head, respectively, said first and second input ports being constructed to introduce electromagnetic radiation of a selected wavelength to the biological tissue through the skull, providing a first detector and a second detector optically connected to a first detection port and a second detection port positioned on the exterior of the head, respectively, said first and second detection ports being constructed to collect through the skull electromagnetic radiation that has migrated in the biological tissue, said sources and detectors being operatively connected to electronic circuitry and a processor, positioning said first input port and said first detection port at a selected relative distance defining a first examined tissue region of the head and brain, positioning said second input port and said second detection port at said relative distance defining a second examined tissue region of the head and brain, said first and second tissue regions being selected to exhibit, for normal tissue, similar scattering or absorptive properties, said first tissue region having normal physiological properties, said second tissue region being examined for pathophysiological change, introducing electromagnetic radiation of said selected wavelength into the head and brain at said first input port and at said second input port, detecting by said first detector radiation that has migrated in the head and brain from said first input port to said first detection port and by said second detector radiation that has migrated in the brain from said second input port to said second detection port, processing signals of said radiation detected by said first and second detectors to create first and second processed data, respectively, said first and second processed data including contribution of absorption or scattering of said introduced radiation due to the skull and the scalp or skin, and determining pathophysiological change in said second tissue region by correlating said processed first and second data.

2. The method of claim 1 wherein said first input port and said first detection port are located on one parietal bone, separated by said distance, so that said first examined tissue region is substantially localized in one hemisphere of the brain, and said second input port and said second detection port are located on the other parietal bone, separated by said distance, so that said second examined tissue region is substantially localized in the other hemisphere of the brain.

3. The method of claim 1 wherein said first input port and said first detection port are located on one temporal bone, separated by said distance, so that said first examined tissue region is substantially localized in one hemisphere of the brain, and said second input port and said second detection port are located on the other temporal bone, separated by said distance, so that said second examined tissue region is substantially localized in the other hemisphere of the brain.

4. The method of claim 1, 2 or 3 wherein said step of correlating said first and second processed data includes creating data representing a differential signal.

5. The method of claim 4 wherein said pathophysiological changes include bleeding or a tumor.

6. The method of claim 1 wherein said first tissue region and said second tissue region are symmetrical regions of the brain.

7. A method of in vivo examination of biological tissue by measuring changes in electromagnetic radiation scattered and absorbed in migration paths in said tissue, comprising providing at least one light source connected to two input ports and at least one detector connected to two detection ports, said source and detector being operatively connected to electronic circuitry and a processor, said input ports being constructed to introduce electromagnetic radiation of a selected wavelength to the skin of the biological tissue and said detection ports being constructed to collect radiation that has migrated in the tissue to another skin location, placing said first input port and said first detection port at a selected relative distance defining a first localized tissue of interest, and placing said second input port and said second detection port at said relative distance defining a second localized tissue of interest, said first and said second localized tissue of interest being selected to exhibit, for normal tissue, similar scattering or absorptive properties, said first localized tissue of interest having normal physiological properties, said second localized tissue of interest being examined for pathophysiological change, introducing electromagnetic radiation of a selected wavelength into the tissue at said first input port, detecting by said first detector radiation of said selected wavelength that has migrated in the first localized tissue of interest from said first input port to said first detection port, introducing electromagnetic radiation of said selected wavelength into the tissue at said second input port, detecting by said second detector radiation of said selected wavelength that has migrated in the second localized tissue of interest and through the skin from said second input port to said second detection port, said first localized tissue of interest having normal physiological properties, said second localized tissue of interest being examined for pathophysiological change, processing signals of said detected radiation that has migrated in said first and second localized tissues of interest to create first and second processed data, said first and second processed data including contribution of absorption or scattering of said introduced radiation by the skin, and determining pathophysiological change in said second localized tissue of interest by correlating both said first and said second processed data.

8. The method of claim 7 wherein said radiation is simultaneously introduced at said first and second input ports and detected at said first and second detection ports.

9. The method of claim 7 or 8 wherein said pathophysiological change includes blood volume change or hemoglobin oxygenation change of the examined tissue.

10. The method of claim 7 or 8 wherein the examined tissue is brain tissue and said determined pathophysiological change includes bleeding or a tumor.

11. The method of claim 7 or 8 wherein said first localized tissue of interest and said second localized tissue of interest are symmetrical regions of the right breast and the left breast, respectively.

12. The method of claim 7 or 8 wherein said first localized tissue of interest and said second localized tissue of interest are symmetrical regions of the right and the left arm or leg, respectively.

13. The method of claim 7 or 8 wherein said wavelength is sensitive to an exogenous pigment or an endogenous pigment present in the examined tissue.

14. The method of claim 13 wherein said endogenous pigment is hemoglobin and said pathophysiological change include oxygenation of hemoglobin.

15. The method of claim 7 or 8 further includes the step of changing said distance between said input ports and said detection ports to change the volume of said localized tissue of interest.

16. A spectrophotometer for transcranial examination of biological tissue by measuring changes in electromagnetic radiation scattered and absorbed in migration paths in the tissue, comprising a first light source and a second light source adapted to introduce electromagnetic radiation of a selected wavelength into the brain simultaneously at a first input port and at a second input port, respectively, said first input port and said second input port being placed at a first selected location and a second selected location on the exterior of the head, respectively, a first detection port positionable at a selected location on the exterior of the head and separated by a selected distance from said first input port to define a first region of interest, and a second detection port positionable at a selected location on the exterior of the head and separated by said distance from said second input port to define a second region of interest, said first and second tissue regions exhibiting, for normal tissue, similar scattering or absorptive properties, a first optical detector optically connected to said first detection port and constructed to detect radiation that has migrated through the skull in said first tissue region of interest, and a second optical detector optically connected to said second detection port and constructed to detect radiation that has migrated through the skull in said second tissue region of interest, a processor and electronic circuitry operatively connected to said sources and detectors, said processor adapted to process signals of said radiation detected by said first detector and said second detector to create first and second processed data, respectively, said first processed data corresponding to absorption or scattering by the skull and biological tissue having normal physiological properties and said second processed data corresponding to absorption or scattering by the skull and biological tissue being examined for pathophysiological change in said second tissue region, and said processor also adapted to determine pathophysiological change in said second tissue region by correlating said processed first and second data.

17. The spectrophotometer of claim 16 wherein said first input port and said first detection port are located on one parietal bone, separated by said distance, so that said first tissue region is substantially localized in one hemisphere of the brain, and said second input port and said second detection port being located on the other parietal bone, separated by said distance, so that said second tissue region is substantially localized in the other hemisphere of the brain.

18. The spectrophotometer of claim 16 wherein said first input port and said first detection port are located on one temporal bone, separated by said distance, so that said first tissue region is substantially localized in one hemisphere of the brain, and said second input port and said second detection port are located on the other temporal bone, separated by said distance, so that said second tissue region is substantially localized in the other hemisphere of the brain.

19. The spectrophotometer of claim 17 or 18 wherein said processor is further adapted to create differential data, representing a differential signal, said differential data being used to determine said pathophysiological change.

20. The spectrophotometer of claim 17 or 18 wherein said processor includes a Fourier transformer.

21. The spectrophotometer of claim 17 or 18 wherein said first detector and said second detector are silicon diodes each having and interference filter adapted to detect said radiation of said selected wavelength.

22. The spectrophotometer of claim 17 or 18 wherein said first detector and said second detector include light-to-frequency convertors each having an interference filter adapted to detect said radiation of said selected wavelength.

23. The spectrophotometer of claim 17 or 18 wherein each said detector includes a light-to-frequency convertor and said processor comprises (a) differential counter adapted to register differential signals received from said light-to-frequency convertors, (b) clocking means adapted to route signals of said detected radiation from said light-to-frequency convertors to said differential counter, and (c) a frequency-to-voltage converter adapted to convert signals from said differential counter.

24. The spectrophotometer of claim 23 wherein said processor further comprises a fast Fourier transformer adapted to process differential signal from said frequency-to-voltage converter.

25. A spectrophotometer for in vivo tissue examination by measuring changes in electromagnetic radiation scattered and absorbed in migration paths in biological tissue, comprising a first input port and a first detection port separated by a selected distance and adapted to be placed at selected locations of the tissue that define a first examined tissue region, a second input port and a second detection port separated by said distance and adapted to be placed at selected locations of the tissue that define a second examined tissue region, said first and second tissue regions exhibiting for normal tissue similar scattering or absorptive properties, at least one light source, optically connected to said two input ports, adapted to introduce electromagnetic radiation of a selected wavelength into the tissue at said first input port and at said second input port, at least one detector, optically connected to said two detection ports, adapted to detect at said first detection port radiation of said wavelength that has migrated in the first examined tissue region from said first input port to said first detection port and at a second detection port radiation of said wavelength that has migrated in the second examined tissue region from said second input port to said second detection port, a processor and electronic circuitry connected to said detector, said processor arranged to process signals of said radiation detected by said first detector and said second detector to create first and second processed data, respectively, said first processed data corresponding to absorption or scattering by the skin and tissue having normal physiological properties and said second processed data corresponding to absorption or scattering by the skin and tissue being examined for pathophysiological change in said second tissue region, and said processor also arranged to determine pathophysiological change in said second tissue of interest by correlating said processed first and second data.

26. The spectrophotometer of claim 25 further comprising a second source and a second detector, each said source being connected to the corresponding input port and each said detector being connected to the corresponding detection port, said processor receiving signals of said detected radiation from said first detector and said second detector.

27. The spectrophotometer of claim 25 wherein said processor is further adapted to compare said radiation detected at said first and second detection ports to create differential data, representing a differential signal, said differential data being used to determine said selected property of the examined tissue.

28. The spectrophotometer of claim 25, 26 or 27 wherein said pathophysiological changes include changes in a blood volume or hemoglobin oxygenation.

29. The spectrophotometer of claim 25, 26 or 27 wherein said first tissue region and said second tissue region are symmetrical regions of the right breast and the left breast, respectively.

30. The spectrophotometer of claim 25, 26 or 27 wherein said first tissue region and said second tissue region are symmetrical regions of the brain.

31. The spectrophotometer of claim 25, 26 or 27 wherein said first tissue region and said second tissue region are symmetrical regions of the right and the left arm or leg, respectively.

32. The spectrophotometer of claim 25, 26 or 27 wherein said source is constructed to emit a wavelength sensitive to an exogenous pigment or an endogenous pigment present in the examined tissue.

33. The spectrophotometer of claim 32 wherein said endogenous pigment is hemoglobin and said pathophysiological change include oxygenation of hemoglobin.

34. The spectrophotometer of claim 25, 26 or 27 further includes an adjustable mechanism constructed to vary the distance between said input ports and said detection ports.

* * * * *